(12) United States Patent
Gonzalez et al.

(10) Patent No.: US 9,926,529 B2
(45) Date of Patent: Mar. 27, 2018

(54) DERIVATION OF NEURAL STEM CELLS AND DOPAMINERGIC NEURONS FROM HUMAN PLURIPOTENT STEM CELLS

(71) Applicant: International Stem Cell Corporation, Carlsbad, CA (US)

(72) Inventors: Rodolfo Gonzalez, Carlsbad, CA (US); Ibon Garitaonandia, Carlsbad, CA (US); Ruslan Semechkin, Carlsbad, CA (US)

(73) Assignee: International Stem Cell Corporation, Carlsbad, CA (US)

(*) Notice: Subject to any disclaimer, the term of this patent is extended or adjusted under 35 U.S.C. 154(b) by 146 days.

(21) Appl. No.: 14/396,180

(22) PCT Filed: Apr. 23, 2013

(86) PCT No.: PCT/US2013/037860
§ 371 (c)(1),
(2) Date: Oct. 22, 2014

(87) PCT Pub. No.: WO2013/163228
PCT Pub. Date: Oct. 31, 2013

(65) Prior Publication Data
US 2015/0087541 A1 Mar. 26, 2015

Related U.S. Application Data

(60) Provisional application No. 61/637,784, filed on Apr. 24, 2012, provisional application No. 61/637,797, filed on Apr. 24, 2012.

(51) Int. Cl.
*C12N 5/0797* (2010.01)
*C12N 5/0793* (2010.01)

(52) U.S. Cl.
CPC ......... *C12N 5/0623* (2013.01); *C12N 5/0619* (2013.01); *C12N 2501/11* (2013.01); *C12N 2501/115* (2013.01); *C12N 2501/119* (2013.01); *C12N 2501/155* (2013.01); *C12N 2501/39* (2013.01); *C12N 2501/727* (2013.01); *C12N 2501/999* (2013.01); *C12N 2506/02* (2013.01); *C12N 2506/45* (2013.01)

(58) Field of Classification Search
CPC .................................................. C12N 5/0623
See application file for complete search history.

(56) References Cited

U.S. PATENT DOCUMENTS

| 7,888,326 | B2 | 2/2011 | Greene | |
|---|---|---|---|---|
| 7,973,031 | B2* | 7/2011 | Griffin | A61K 31/407 514/211.08 |
| 2009/0018096 | A1 | 1/2009 | Greene | |
| 2009/0291134 | A1 | 11/2009 | Ahmad et al. | |
| 2011/0217774 | A1 | 9/2011 | Kim et al. | |
| 2013/0280809 | A1* | 10/2013 | Efe | C12N 5/0602 435/467 |

FOREIGN PATENT DOCUMENTS

| JP | 2012-501194 | | 1/2012 | |
|---|---|---|---|---|
| WO | WO 2009/143421 A2 | | 11/2009 | |
| WO | WO2011/019092 | * | 2/2011 | C12N 5/07 |
| WO | WO 2011/019092 A1 | | 2/2011 | |

OTHER PUBLICATIONS

Zhu et al. (Cell Stem Cell. 2009; 4: 416-426).*
Zhou et al. (Stem Cells. 2010; 28:1741-1750).*
Zhao et al. (The Journal of Biological Chemistry. Nov. 29, 2002; 277(48): 46609-46615).*
Frosina, Guido, "Frontiers in Targeting Glioma Stem Cells," *Eur. J. Cancer* (2011), 47:496-507, Elsevier Ltd.
Hao et al., "In vivo Structure Activity Relationship Study of Dorsomorphin Analogs Identifies Selective VEGF and BMP Inhibitors," *ACS Chem. Biol.* (2010), 5(2):245-253.
Shiras et al., "Spontaneous Transformation of Human Adult Nontumorigenic Stem Cells to Cancer Stem Cells Is Driven by Genomic Instability in a Human Model of Glioblastoma," *Stem Cells* (2007), 25:1478-1489.
Gonzalez, Rodolfo et al.: "*Deriving dopaminergic neurons for clinical use. A practical approach*", Scientific Reports, Mar. 15, 2013, vol. 3 : 1463, 6 pgs.
Laco, Filip et al.: "*Cardiomyocyte differentiation of pluripotent stem cells with SB203580 analogues correlates with Wnt pathway CK1 inhibition independent of p38 MAPK signaling*"; J. Molecular & Cellular Cardiology, Mar. 1, 2015, vol. 80, pp. 56-70.
Morizane, Asuka et al.: "*Small-molecule inhibitors of bone morphogenic protein and activin/nodal signals promote highly efficient neural induction from human pluripotent stem cells*", J. Neurosciences Reserch, vol. 89, No. 2, Dec. 8, 2010, pp. 117-126.

(Continued)

*Primary Examiner* — Scott Long
(74) *Attorney, Agent, or Firm* — DLA Piper LLP (US)

(57) ABSTRACT

The present invention is based in part on a chemically defined method of generating neural stem cells (NSCs) and dopaminergic (DA) neurons from human pluripotent stem cells (hPSCs). The DA neurons of the invention can be derived from hPSCs and NSCs. The present invention also provides reagents and kits useful for the derivation of neural stem cells and dopaminergic neurons from human pluripotent stem cells.

2 Claims, 6 Drawing Sheets

(56) References Cited

OTHER PUBLICATIONS

Extended European Search Report dated Nov. 23, 2015, regarding EP 13 78 2178.
Bruggeman, SWM, et al.: "*Ink4a and Arf differentially affect cell proliferation and neural stem cell selfrenewal in Bmil-deficient mice*"; Genes Dev. 2005; 19: 1438-1443.
Korzhevskii, D.E. et al.: "*Neutral Markers in Investigation Stem Cells Differentiation*"; Genes and Cells, 2010; V(3): 57-63. (English Abstract).
Roque, T: "*Lack of a $p21^{waf1/Cip}$ Dependent G1/S Checkpoint in Neural Stem and Progenitor Cells After DNA Damage In Vivo*"; Stem Cells, 2012; 30(3): 537-547.
Russian Office Action dated May 30, 2017, regarding RU 2014147015.
Japanese Office Action dated Mar. 29, 2017, regarding JP 2015-509088.

\* cited by examiner

DERIVATION OF NEURAL STEM CELLS AND DOPAMINERGIC NEURONS FROM HUMAN PLURIPOTENT STEM CELLS

CROSS-REFERENCE TO RELATED APPLICATIONS

This application is a 35 USC § 371 National Stage application of International Application No. PCT/US2013/037860 filed Apr. 23, 2013, now pending; which claims the benefit under 35 USC § 119(e) to U.S. Application Ser. No. 61/637,797 filed Apr. 24, 2012 and to U.S. Application Ser. No. 61/637,784 filed Apr. 24, 2012, both now expired. The disclosure of each of the prior applications is considered part of and is incorporated by reference in the disclosure of this application.

FIELD OF THE INVENTION

The present invention relates generally to stem cells and more specifically to methods for deriving neural stem cells and dopaminergic neurons from human pluripotent stem cells.

BACKGROUND INFORMATION

Human embryonic stem cells (ES) cells are pluripotent cells that can differentiate into a large array of cell types. Stem cells are distinguished from other cell types by two important characteristics. First, they are unspecialized cells capable of renewing themselves through cell division, sometimes after long periods of inactivity. Second, under certain physiologic or experimental conditions, they can be induced to become tissue- or organ-specific cells with special functions. In some organs, such as the gut and bone marrow, stem cells regularly divide to repair and replace worn out or damaged tissues. In other organs, however, such as the pancreas and the heart, stem cells only divide under special conditions.

During embryonic development, stem cells form the tissues of the body from three major cell populations: ectoderm, mesoderm and definitive endoderm. Mesoderm gives rise to blood cells, endothelial cells, cardiac and skeletal muscle, and adipocytes. Definitive endoderm generates liver, pancreas and lung. Ectoderm gives rise to the nervous system, skin and adrenal tissues.

A potential application of stem cells, is making cells and tissues for medical therapies. Today, donated organs and tissues are often used to replace those that are diseased or destroyed. Unfortunately, the number of people needing a transplant far exceeds the number of organs available for transplantation. Stem cells offer the possibility of a renewable source of replacement cells and tissues to treat a myriad of diseases, conditions, and disabilities including Parkinson's disease, amyotrophic lateral sclerosis, spinal cord injury, burns, heart disease, diabetes, and arthritis.

Parkinson's disease (PD) is a neurological disorder caused by a progressive degeneration of midbrain dopamine (DA) neurons in the substantia nigra pars compacta. The degeneration of DA neurons causes a gradual dysfunction of the motor system leading to symptoms such as tremor, rigidity, and bradykinesia, among others. There is currently no cure for PD and although treatments such as deep brain stimulation and levodopa can alleviate some of the symptoms, they tend to lose efficacy over time. However, the localized nature of the loss of DA neurons in the substantia nigra (SN) makes cell replacement therapy an attractive approach to treating Parkinson's disease (PD) patients. Implantation of neuronal cells such as neural stem cells (NSCs) and DA neurons have already been shown to improve the motor symptoms in PD animal models. In order for stem cell based therapies for PD to become a reality it is critical to be able to generate a homogeneous population of NSCs which will in turn generate functional DA neurons either in situ or in vitro, depending on whether the terminal differentiation occurs in the patient's brain or in culture.

SUMMARY OF THE INVENTION

The present invention is based in part on a chemically defined method of generating neural stem cells (NSCs) and dopaminergic (DA) neurons from human pluripotent stem cells (hPSCs). The DA neurons of the invention can be derived from hPSCs and NSCs. The present invention also provides reagents and kits useful for the derivation of neural stem cells and dopaminergic neurons from human pluripotent stem cells.

The present invention provides for the derivation of neural stem cells (NSCs) by treating human pluripotent stem cells (hPSCs) with at least one neural stem cell induction compound and assaying the cells for neural stem cell markers. The present invention also provides for the derivation of a high-purity population of DA neurons from hPSCs in a robust and reproducible manner via a stable NSC stage, where the cells can be expanded and cryopreserved, using newly developed chemically directed differentiation methods.

In one embodiment, the present invention provides a method to generate neural stem cells (NSCs). The method includes treating human pluripotent stem cells (hPSCs) with a checkpoint kinase 1 (CK1) inhibitor and a bone morphogenic protein (BMP) inhibitor and analyzing the cells for neural stem cell markers. In a one aspect, the CK1 inhibitor is SB218078. In an additional aspect, the BMP inhibitor may be Dorsomorphin, LD-193189 or DMH-1. In specific aspects, the CK1 inhibitor is SB218078 and the BMP inhibitor is Dorsomorphin; the CK1 inhibitor is SB218078 and the BMP inhibitor is LD-193189; and the CK1 inhibitor is SB218078 and the BMP inhibitor is DMH-1.

In an aspect, the hPSCs are human embryonic stem cells (hESCs), human parthenogenetic stem cells (hpSCs) or induced pluripotent stem cells (iPSCs), or cell lines derived therefrom.

In one aspect, the neural stem cell markers include BRN2, CD113, CD15, CXCR4, DCX, FABP7, FOXA2, FOXO4, GFAP, LMX1A, Musashi-1, MAP2, Nestin, OTX2, PAX6, TUBB3, SOX1, SOX2, SOX3 or ST6GALNAC5 or any combination thereof.

In another aspect, the hPSCs are treated with SB218078 and DMH-1. The resulting NCSs express LMX1A and FOX2A and are ventral midbrain neuroectodermal cells. The ventral midbrain neuroectodermal cells are precursors to dopaminergic neurons.

In one embodiment, the present invention provides for neural stem cells (NSCs). The subject NSCs are generated by treating human pluripotent stem cells (hPSCs) with a checkpoint kinase 1 (CK1) inhibitor and a bone morphogenic protein (BMP) inhibitor and analyzing the cells for neural stem cell markers. In one aspect, the CK1 inhibitor is SB218078. In an additional aspect, the BMP inhibitor may be Dorsomorphin, LD-193189 or DMH-1. In specific aspects, the CK1 inhibitor is SB218078 and the BMP inhibitor is Dorsomorphin; the CK1 inhibitor is SB218078 and the BMP inhibitor is LD-193189; and the CK1 inhibitor is SB218078 and the BMP inhibitor is DMH-1.

In an aspect, the hPSCs are human embryonic stem cells (hESCs), human parthenogenetic stem cells (hpSCs) or induced pluripotent stem cells (iPSCs), or cell lines derived therefrom.

In another embodiment, the present invention provides a method to generate dopaminergic neurons. The method includes treating human pluripotent stem cells (hPSCs) with a checkpoint kinase 1 (CK1) inhibitor and a bone morphogenic protein (BMP) inhibitor, identifying neural stem cells by assaying the treated hPSCs for neural stem cell markers, treating NSCs with at least one dopaminergic neuron inducing compound and analyzing cells for dopaminergic neuron cell markers. In certain aspects, the CK1 inhibitor is SB218078 and the BMP inhibitor is Dorsomorphin, LD-193189 or DMH-1. In a preferred aspect, the CK1 inhibitor is SB218078 and the BMP inhibitor is DMH-1.

In an aspect, the hPSCs are human embryonic stem cells (hESCs), human parthenogenetic stem cells (hpSCs) or induced pluripotent stem cells (iPSCs), or cell lines derived therefrom.

In one aspect of the method, the neural stem cell markers maybe BRN2, CD113, CD15, CXCR4, DCX, FABP7, FOXA2, FOXO4, GFAP, LMX1A, Musashi-1, MAP2, Nestin, OTX2, PAX6, TUBB3, SOX1, SOX2, SOX3 or ST6GALNAC5 or any combination thereof.

In certain aspects of the method, the dopaminergic neuron inducing compound maybe Homoquinolinic acid, L-Cysteinesulfinic acid, Kynurenic acid, (R)-(+)-HA-966, m-Chlorophenylbiguanide hydrochloride, Calpeptin, Dimaprit dihydrochloride, 8-Hydroxy-DPAT hydrobromide, trans-4-Hydroxycrotonic acid, Fasudil hydrochloride, Thioperamide, Retinoic acid, AM580, TTNPB, Remoxipride hydrochloride, ICI 215,001 hydrochloride, Imiloxan hydrochloride, Spiperone hydrochloride, Kenpaullone, CL 218872, CV 1808, Ro 15-4513, Linopirdine dihydrochloride, Guggulsterone, Ch 55, 3-MATIDA, SEW 2871, Immethridine dihydrobromide, LY 364947, Tranylcypromine hydrochloride, (−)-Cytisine or Nilutamide, or any combination thereof. In a preferred aspect, the dopaminergic neuron inducing compound is Guggulsterone.

In an additional aspect of the method, the dopaminergic neuron cell markers maybe TUJ1, TH, Dat, Foxa2, Nurr-1, Girk2, MAPT, SYT4, FOXA1, DDC, ASCL1, PINK1, PAX5, LMX1B, PITX3, NURR-1, LMX1A, EN1, PAX2, TFF3, PITX2, DCX, MAP2, PITX1 or VMAT2, or any combination thereof.

In a further embodiment, the present invention provides for dopaminergic neurons. The subject DA neurons are generated by treating human pluripotent stem cells (hPSCs) with a checkpoint kinase 1 (CK1) inhibitor and a bone morphogenic protein (BMP) inhibitor, identifying neural stem cells by assaying the treated hPSCs for neural stem cell markers, treating NSCs with at least one dopaminergic neuron inducing compound and analyzing cells for dopaminergic neuron cell markers. In certain aspects, the CK1 inhibitor is SB218078 and the BMP inhibitor is Dorsomorphin, LD-193189 or DMH-1. In a preferred aspect, the CK1 inhibitor is SB218078 and the BMP inhibitor is DMH-1.

In an aspect, the hPSCs are human embryonic stem cells (hESCs), human parthenogenetic stem cells (hpSCs) or induced pluripotent stem cells (iPSCs), or cell lines derived therefrom.

In one aspect of the method, the neural stem cell markers maybe BRN2, CD113, CD15, CXCR4, DCX, FABP7, FOXA2, FOXO4, GFAP, LMX1A, Musashi-1, MAP2, Nestin, OTX2, PAX6, TUBB3, SOX1, SOX2, SOX3 or ST6GALNAC5, or any combination thereof.

In a further aspect of the method, the dopaminergic neuron inducing compound maybe Homoquinolinic acid, L-Cysteinesulfinic acid, Kynurenic acid, (R)-(+)-HA-966, m-Chlorophenylbiguanide hydrochloride, Calpeptin, Dimaprit dihydrochloride, 8-Hydroxy-DPAT hydrobromide, trans-4-Hydroxycrotonic acid, Fasudil hydrochloride, Thioperamide, Retinoic acid, AM580, TTNPB, Remoxipride hydrochloride, ICI 215,001 hydrochloride, Imiloxan hydrochloride, Spiperone hydrochloride, Kenpaullone, CL 218872, CV 1808, Ro 15-4513, Linopirdine dihydrochloride, Guggulsterone, Ch 55, 3-MATIDA, SEW 2871, Immethridine dihydrobromide, LY 364947, Tranylcypromine hydrochloride, (−)-Cytisine or Nilutamide, or any combination thereof. In a preferred aspect, the dopaminergic neuron inducing compound is Guggulsterone.

In an additional aspect of the method, the dopaminergic neuron cell markers maybe TUJ1, TH, Dat, Foxa2, Nurr-1, Girk2, MAPT, SYT4, FOXA1, DDC, ASCL1, PINK1, PAX5, LMX1B, PITX3, NURR-1, LMX1A, EN1, PAX2, TFF3, PITX2, DCX, MAP2, PITX1 or VMAT2, or any combination thereof.

In another embodiment, the present invention provides a kit for the derivation of NSCs. The kit may include a checkpoint kinase 1 (CK1) inhibitor and a bone morphogenic protein (BMP) inhibitor, reagents to identify neural stem cell markers and directions for the generation of NSCs from hPSCs. In one aspect, the CK1 inhibitor is SB218078 and the BMP inhibitor is Dorsomorphin, LD-193189 or DMH-1. In certain aspects the CK1 inhibitor is SB218078 and the BMP inhibitor is Dorsomorphin; CK1 inhibitor is SB218078 and the BMP inhibitor is LD-193189; CK1 inhibitor is SB218078 and the BMP is DMH-1. The kit may include reagents to identify BRN2, CD113, CD15, CXCR4, DCX, FABP7, FOXA2, FOXO4, GFAP, LMX1A, Musashi-1, MAP2, Nestin, OTX2, PAX6, TUBB3, SOX1, SOX2, SOX3 or ST6GALNAC5 neural stem cell markers.

In another embodiment, the present invention provides a kit for the production of dopaminergic neurons. The kit includes checkpoint kinase 1 (CK1) inhibitor and a bone morphogenic protein (BMP) inhibitor, reagents to identify neural stem cell markers, at least one dopaminergic neuron inducing compound, reagents to identify dopaminergic neuron cell markers and directions for the production of dopaminergic neurons from hPSCs. In one aspect, the CK1 inhibitor is SB218078, the BMP inhibitor is DMH-1 and the dopaminergic neuron inducing compound is Gugglesterone. The kit may include reagents to identify BRN2, CD113, CD15, CXCR4, DCX, FABP7, FOXA2, FOXO4, GFAP, LMX1A, Musashi-1, MAP2, Nestin, OTX2, PAX6, TUBB3, SOX1, SOX2, SOX3 or ST6GALNAC5 neural stem cell markers. The kit may also include reagents to identify TUJ1, TH, Dat, Foxa2, Nurr-1, Girk2, MAPT, SYT4, FOXA1, DDC, ASCL1, PINK1, PAX5, LMX1B, PITX3, NURR-1, LMX1A, EN1, PAX2, TFF3, PITX2, DCX, MAP2, PITX1 or VMAT2 dopaminergic neuron cell markers.

In an additional embodiment, the present invention provides a method of treatment for neurological diseases and disorders. The method includes the administration of NSCs to a subject with a neurological disease or disorder.

In a further embodiment, the present invention provides a method of treating neurological diseases and disorders. The method includes the administration of NSCs or DA neurons to a subject with a neurological disease or disorder.

DETAILED DESCRIPTION OF THE INVENTION

Figure 1:
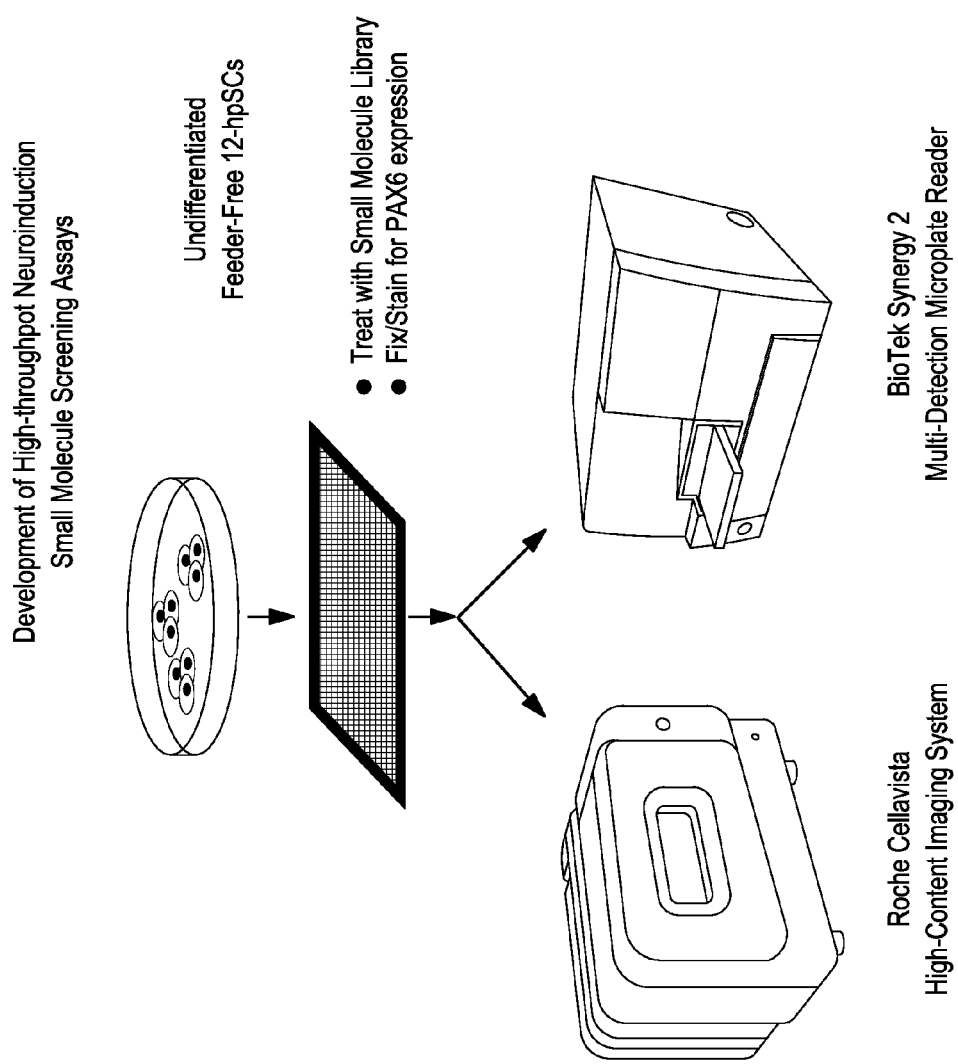
FIG. 1 depicts the high-through put neuroindiction small molecule screening assay. Undifferentiated feeder free hPSCs are plated in a 96 well plate, treated with small molecules, then fixed and stained for PAX6 expression.
Figure 2:
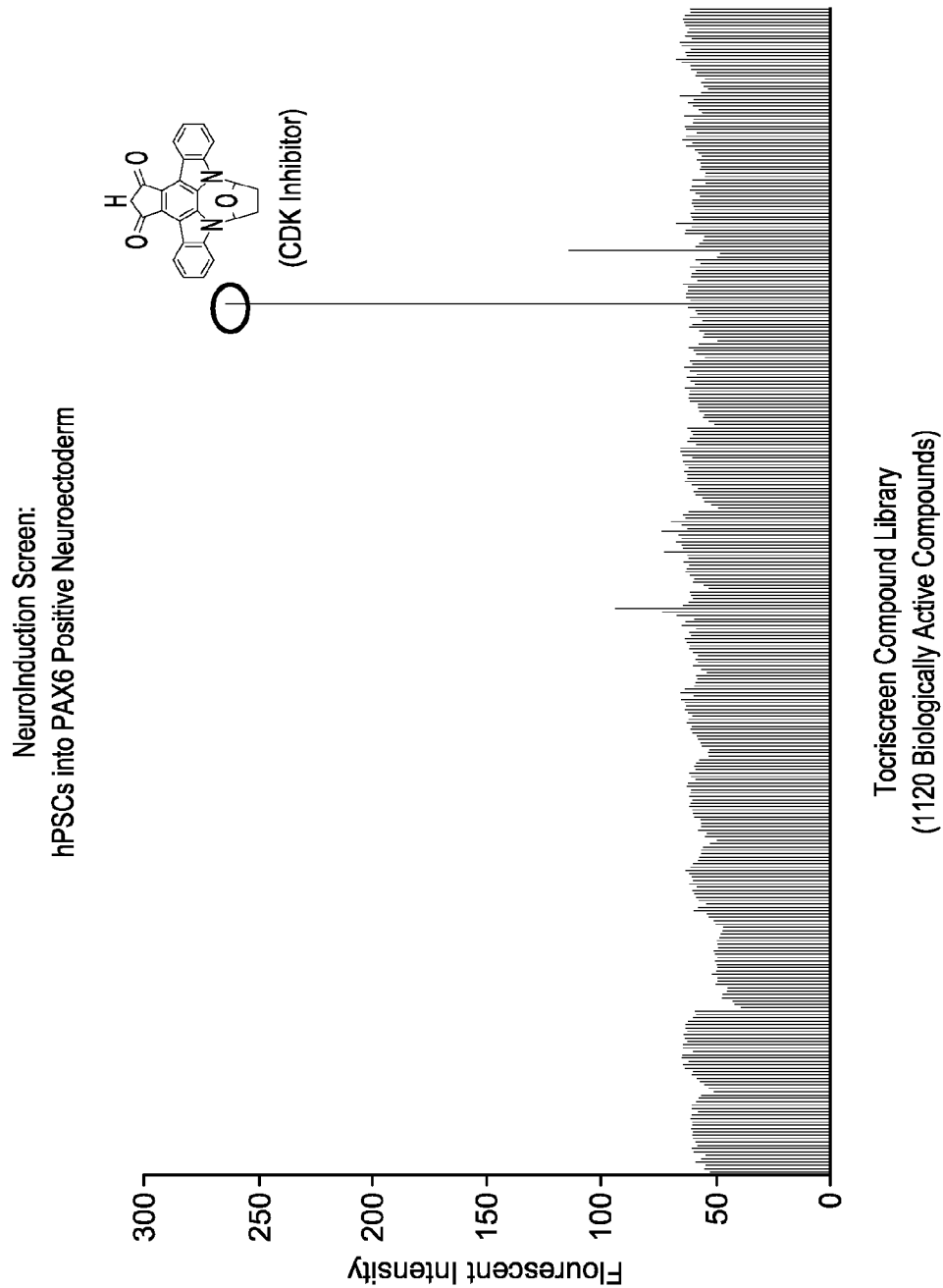
FIG. 2 is a graph showing the screening of the small molecule treated hPSCs for PAX6 expression. Treatment with SB218078 in combination with Dorsomorphin produced high expression of PAX6.

The present invention is based in part on a method of generating neural stem cells (NSCs) and dopaminergic (DA) neurons from human pluripotent stem cells (hPSCs). The DA neurons of the invention can be derived from hPSCs and NSCs. The present invention also provides reagents and kits useful for the derivation of neural stem cells and dopaminergic neurons from human pluripotent stem cells.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The present invention provides for the derivation of neural stem cells (NSCs) by treating hPSCs with at least one neural stem cell induction compound and assaying the cells for neural stem cell markers. The present invention also provides for the derivation of a high-purity population of DA neurons from hPSCs in a robust and reproducible manner via a stable NSC stage, where the cells can be expanded and cryopreserved, using newly developed chemically directed differentiation methods.

Generation of neural stem cells (NSCs) from human pluripotent stem cells (hPSCs), including but not limited to human embryonic stem cells (hESCs), human parthenogenetic stem cells (hpSCs), induced pluripotent stem cells (iPSCs), is a vital component of cell-based strategies for treatment of neurological diseases. Before hPSC-derived NSCs can be administered in therapeutic modalities, however, chemically defined culture conditions must be developed that reproducibly and robustly induce the generation of NSCs. Here, a high-throughput screen was performed to identify small molecules that induce the differentiation of hPSCs to NSCs. The small molecule SB218078, a reported inhibitor of checkpoint kinase 1 (CK1), was identified from the screen and used to develop a chemically defined differentiation method to differentiate hPSCs into NSCs.

The chemical method reported herein provides for the generation of a homogenous population of NSCs from hPSCs that can be further differentiated into mature neurons for cell therapies or drug discovery.

Generation of dopaminergic cells (DCs) from human pluripotent stem cells (hPSCs), including but not limited to human embryonic stem cells (hESC), human parthenogenetic stem cells (hpSCs), induced pluripotent stem cells (iPSCs), is a vital component of cell-based strategies for treatment of Parkinson disease. Before hPSC-derived DCs can be administered in therapeutic modalities, however, chemically defined culture conditions must be developed that reproducibly and robustly induce dopaminergic cell differentiation. A high-throughput screen was perform to identify small molecules that induce the differentiation of hPSCs derived Neural Stem Cells (hPSC-NSCs) into dopaminergic (DA) neurons. Small molecules were identified from the screen and then used to develop a chemically defined differentiation method to differentiate hPSCs-NSCs into dopaminergic cells.

The chemical method reported herein provides instructions for the generation of dopaminergic neurons from hPSCs that can be used for neurological disease cellular therapy, such as Parkinson's disease, or drug discovery. Additionally, small molecules reported herein as inducers of dopaminergic cell differentiation were found to have potent in vitro human dopamine neuron neuroprotective effects and can be used for the prevention and/or progression of neurological diseases, such as Parkinson disease.

New small molecules that regulate the step-wise differentiation of human pluripotent stem cells into DA neurons have been identified. The steroid, guggulsterone, was found to be the most effective inducer of neural stem cells into DA neurons. These neurons are extensively characterized and shown to be functional. This new approach offers a practical route to creating neurons of sufficient quality to be used to treat neurological disease patients.

The methods of deriving neural stem cells (NSCs), dopaminergic (DA) neurons and the resulting stem cells and neurons that are described herein are generated from human pluripotent stem cells (hPSCs), such as embryonic stem cells. As used herein, "embryonic" refers to a range of developmental stages of an organism beginning with a single zygote and ending with a multicellular structure that no longer comprises pluripotent or totipotent cells other than developed gametic cells. In addition to embryos derived by gamete fusion, the term "embryonic" refers to embryos derived by somatic cell nuclear transfer. Human stem cells can be maintained in culture in a pluripotent state without substantial differentiation using methods that are known in the art. Such methods are described, for example, in U.S. Pat. Nos. 5,453,357, 5,670,372, 5,690,926 5,843,780, 6,200,806 and 6,251,671 the disclosures of which are incorporated herein by reference in their entireties.

As used herein, "multipotent" or "multipotent cell" refers to a cell type that can give rise to a limited number of other particular cell types. Examples of multipotent cells include ectodermal cells, endodermal cells, mesodermal cells and neural stem cells which can give rise to limited number of other cells.

As used herein, a "pluripotent cell" refers to a cell that can be maintained in vitro for prolonged, theoretically indefinite period of time in an undifferentiated state, that can give rise to different differentiated tissue types, i.e., ectoderm, mesoderm, and endoderm. Human pluripotent stem cells (hPSCs) include, but are not limited to, human embryonic stem cells (hESCs), human parthenogenetic stem cells (hpSCs) and induced pluripotent stem cells (iPSCs). Methods of obtaining such hPSCs are well known in the art.

One method of obtaining hPSCs is by parthenogenesis. "Parthenogenesis" ("parthenogenically activated" and "parthenogenetically activated" is used herein interchangeably) refers to the process by which activation of the oocyte occurs in the absence of sperm penetration, and refers to the development of an early stage embryo comprising trophectoderm and inner cell mass that is obtained by activation of an oocyte or embryonic cell, e.g., blastomere, comprising DNA of all female origin. In a related aspect, a "parthenote" refers to the resulting cell obtained by such activation. In another related aspect, "blastocyst: refers to a cleavage stage of a fertilized of activated oocyte comprising a hollow ball of cells made of outer trophoblast cells and an inner cell mass (ICM). In a further related aspect, "blastocyst formation" refers to the process, after oocyte fertilization or activation, where the oocyte is subsequently cultured in media for a time to enable it to develop into a hollow ball of cells made of outer trophoblast cells and ICM (e.g., 5 to 6 days).

Another method of obtaining hPSCs is through nuclear transfer. As used herein, "nuclear transfer" refers to the fusion or transplantation of a donor cell or DNA from a donor cell into a suitable recipient cell, typically an oocyte of the same or different species that is treated before, concomitant or after transplant or fusion to remove or inactivate its endogenous nuclear DNA. The donor cell used for nuclear transfer include embryonic and differentiated cells, e.g., somatic and germ cells. The donor cell may be in a proliferative cell cycle (G1, G2, S or M) or non-proliferating (G0 or quiescent). Preferably, the donor cell or DNA from the donor cell is derived from a proliferating mammalian cell culture, e.g., a fibroblast cell culture. The donor cell optionally may be transgenic, i.e., it may comprise one or more genetic addition, substitution or deletion modifications.

A further method for obtaining hPSCs is through the reprogramming of cells to obtain induced pluripotent stem cells. Takahashi et al. (Cell 131, 861-872 (2007)) have disclosed methods for reprogramming differentiated cells, without the use of any embryo or ES (embryonic stem) cell, and establishing an inducible pluripotent stem cell having similar pluripotency and growing abilities to those of an ES cell. Takahashi et al. describe various different nuclear reprogramming factors for differentiated fibroblasts, which include products of the following four genes: an Oct family gene; a Sox family gene; a Klf family gene; and a Myc family gene.

The pluripotent state of the cells is preferably maintained by culturing cells under appropriate conditions, for example, by culturing on a fibroblast feeder layer or another feeder layer or culture that includes leukemia inhibitory factor (LIF). The pluripotent state of such cultured cells can be confirmed by various methods, e.g., (i) confirming the expression of markers characteristic of pluripotent cells; (ii) production of chimeric animals that contain cells that express the genotype of the pluripotent cells; (iii) injection of cells into animals, e.g., SCID mice, with the production of different differentiated cell types in vivo; and (iv) observation of the differentiation of the cells (e.g., when cultured in the absence of feeder layer or LIF) into embryoid bodies and other differentiated cell types in vitro.

The pluripotent state of the cells used in the present invention can be confirmed by various methods. For example, the cells can be tested for the presence or absence of characteristic ES cell markers. In the case of human ES cells, examples of such markers are identified supra, and include SSEA-4, SSEA-3, TRA-1-60, TRA-1-81 and OCT 4, and are known in the art.

Also, pluripotency can be confirmed by injecting the cells into a suitable animal, e.g., a SCID mouse, and observing the production of differentiated cells and tissues. Still another method of confirming pluripotency is using the subject pluripotent cells to generate chimeric animals and observing the contribution of the introduced cells to different cell types.

Yet another method of confirming pluripotency is to observe ES cell differentiation into embryoid bodies and other differentiated cell types when cultured under conditions that favor differentiation (e.g., removal of fibroblast feeder layers). This method has been utilized and it has been confirmed that the subject pluripotent cells give rise to embryoid bodies and different differentiated cell types in tissue culture.

The resultant pluripotent cells and cell lines, preferably human pluripotent cells and cell lines have numerous therapeutic and diagnostic applications. Such pluripotent cells may be used for cell transplantation therapies or gene therapy (if genetically modified) in the treatment of numerous disease conditions.

Human pluripotent stem cells (hPSCs) include, but are not limited to, human embryonic stem cells, human parthenogenetic stem cells, induced pluripotent stem cells and cell lines produced by such cells. hPSCs are maintained in culture in a pluripotent state by routine passage until it is desired that neural stem cells be derived.

An "NSC" (also referred to as a "multipotent neural stem cell") exhibits one or more of the following properties: 1) expression of Nestin; 2) expression of Sox2; 3) expression of Musashi1; 4) ability to undergo self-renewal, either as a monolayer or in suspension cultures as neurospheres; 5) ability to differentiate into neurons, specific subtypes of neurons, astrocytes, and oligodendrocytes; and 6) morphological characteristics typical for NSCs.

NSCs are self-renewing, multipotent cells that generate the main phenotypes of the nervous system. NSCs primarily differentiate into neurons, astrocytes, and oligodendrocytes.

Neuroectoderm (or neural ectoderm or neural tube epithelium) is the term for ectoderm which receives Bone Morphogenetic Protein-inhibiting signals from proteins such as noggin, which leads to the development of the nervous system from this tissue. After recruitment from the ectoderm, the neuroectoderm undergoes three stages of development: transformation into the neural plate, transformation into the neural groove (with associated neural folds), and transformation into the neural tube. After formation of the tube, the brain forms into three sections; the hindbrain, the midbrain, and the forebrain.

Neural stem cells can be identified by detecting increased expression of neural stem cell markers, which include, but are not limited to: ABCG2, ASCL1/Mash1, beta-III Tubulin, BMI-1, Brg1, BRN2, CDCP1, CD113, CD15, CXCR4, DCX, FABP, FABP7/B-SLAIN1, FABP8/M-FABP, FGF R4, FOXA2, FOXO4, Frizzled-9, GFAP, Glut1, HOXB1, LMX1A, MAP2, Musashi-1, Musashi-2, Nestin, NeuroD1, Noggin, Notch-1, Notch-2, Nucleostemin, Oligodendrocyte Marker O4, OTX2, PAX6, PDGF R alpha, Prominin 2, SOX1, SOX2, SOX3, SOX9, SOX11, SOX21, SSEA-1, ST6GALNAC5, TUBB3, TRAF-4 and/or Vimentin.

Nestin is a useful marker because although it is expressed predominantly in stem cells of the central nervous system (CNS), its expression is absent from nearly all mature CNS cells. The transcription factor SOX2 is known to be expressed at high levels in the neuroepithelium of the developing CNS and is thought to be centrally important for neural stem cell proliferation and differentiation.

The present invention provides methods for the derivation of neural stem cells (NSCs) by treating hPSCs with at least one neural stem cell induction compound and assaying the cells for neural stem cell markers.

In one embodiment, the present invention provides a method to generate neural stem cells (NSCs). The method includes treating human pluripotent stem cells (hPSCs) with a checkpoint kinase 1 (CK1) inhibitor and a bone morphogenic protein (BMP) inhibitor and analyzing the cells for neural stem cell markers. In a one aspect, the CK1 inhibitor is SB218078. In an additional aspect, the BMP inhibitor may be Dorsomorphin, LD-193189 or DMH-1. In specific aspects, the CK1 inhibitor is SB218078 and the BMP inhibitor is Dorsomorphin; the CK1 inhibitor is SB218078 and the BMP inhibitor is LD-193189; and the CK1 inhibitor is SB218078 and the BMP inhibitor is DMH-1.

In an aspect, the hPSCs are human embryonic stem cells (hESCs), human parthenogenetic stem cells (hpSCs) or induced pluripotent stem cells (iPSCs), or cell lines derived therefrom.

In one aspect, the neural stem cell markers include BRN2, CD113, CD15, CXCR4, DCX, FABP7, FOXA2, FOXO4, GFAP, LMX1A, Musashi-1, MAP2, Nestin, OTX2, PAX6, TUBB3, SOX1, SOX2, SOX3 or ST6GALNAC5, or combinations thereof.

As demonstrated in the Examples, the present invention provides NSCs which express BRN2, CD113, CD15, CXCR4, DCX, FABP7, FOXA2, FOXO4, GFAP, LMX1A, Musashi-1, MAP2, Nestin, OTX2, PAX6, TUBB3, SOX1, SOX2, SOX3 and ST6GALNAC5.

As used herein, "neural stem cell inducing compound" is a compound that induces a hPSCs to become a NSC. Such compounds include, but are not limited to, checkpoint kinase inhibitors and bone morphogenic protein inhibitors.

Checkpoint 1 kinase (Chk1) plays a major role in the regulation of G2 transition during the cell cycle. Three checkpoints in G1, S and G2 are activated in response to DNA damage. DNA lesions can be induced by some chemical agents or by radiation or during DNA replication. The role of the checkpoints is to delay the cell cycle progression when DNA damage occurs in order to provide time for DNA repair. The G1/S checkpoint is p53 dependent. In the presence of DNA damage, a rapid induction of p53 activity occurs, inducing cyclin-dependent kinases inhibition and cell cycle arrest to prevent the replication of damaged DNA during the S phase. In the p53-mutated cells, in which the G1 checkpoint is lacking, only the G2 checkpoint is able to provide a delay in the cell cycle progression allowing the activation of DNA repair pathways. Chk1 inhibitors abrogate the G2 checkpoint.

Examples of CK1 inhibitors include, but are not limited to, SB-218078, Hymenialdisine, Debromohymenialdisine, PD 0166285, 13-Hydroxy-15-oxozoapat line, granulatimide, isogranulatimide, and S27888.

Bone morphogenetic proteins (BMPs) are multi-functional growth factors that belong to the transforming growth factor beta (TGFβ) superfamily. Originally discovered by their ability to induce the formation of bone and cartilage, BMPs are now considered to constitute a group of pivotal morphogenetic signals, orchestrating tissue architecture throughout the body. BMPs interact with specific receptors on the cell surface, referred to as bone morphogenetic protein receptors (BMPRs). Signal transduction through BMPRs results in mobilization of members of the SMAD family of proteins. The signaling pathways involving BMPs, BMPRs and Smads are important in the development of the heart, central nervous system, and cartilage, as well as post-natal bone development. They have an important role during embryonic development on the embryonic patterning and early skeletal formation. BMP signaling plays critical roles in heart, neural and cartilage development.

Examples of BMP inhibitors include, but are not limited to, Dorsomorphin, LD-193189 and DMH-1.

NSCs derived from hPSCs can be readily identified using methods well known to one of skill in the art. These methods include identifying neural stem cell markers using immunohistochemistry, FACS analysis and measurement of RNA expression levels.

In one embodiment, the present invention provides for neural stem cells. The subject NSCs are generated by treating human pluripotent stem cells (hPSCs) with a checkpoint kinase 1 (CK1) inhibitor and a bone morphogenic protein (BMP) inhibitor and analyzing the cells for neural stem cell markers. In one aspect, the CK1 inhibitor is SB218078. In an additional aspect, the BMP inhibitor may be Dorsomorphin, LD-193189 or DMH-1. In specific aspects, the CK1 inhibitor is SB218078 and the BMP inhibitor is Dorsomorphin; the CK1 inhibitor is SB218078 and the BMP inhibitor is LD-193189; and the CK1 inhibitor is SB218078 and the BMP inhibitor is DMH-1.

In an aspect, the hPSCs are human embryonic stem cells (hESCs), human parthenogenetic stem cells (hpSCs) or induced pluripotent stem cells (iPSCs), or cell lines derived therefrom.

In one aspect, the NSCs express neural stem cell markers which may be BRN2, CD113, CD15, CXCR4, DCX, FABP7, FOXA2, FOXO4, GFAP, LMX1A, Musashi-1, MAP2, Nestin, OTX2, PAX6, TUBB3, SOX1, SOX2, SOX3 and ST6GALNAC5, or any combination thereof.

In another aspect, the hPSCs are treated with SB218078 and DMH-1. The resulting NCSs express LMX1A and FOX2A and are ventral midbrain neuroectodermal cells. The ventral midbrain neuroectodermal cells are precursors to dopaminergic neurons.

Once NSCs are derived, the cells may be maintained in vitro for prolonged, theoretically indefinite periods of time retaining the ability to differentiate into other neural cell types, such as astrocytes, neurons and oligodendrocytes. As described in the Examples, hPSCs derived NSCs can be grown on Matrigel coated plates in NSC medium for at least seven passages.

Figure 3:
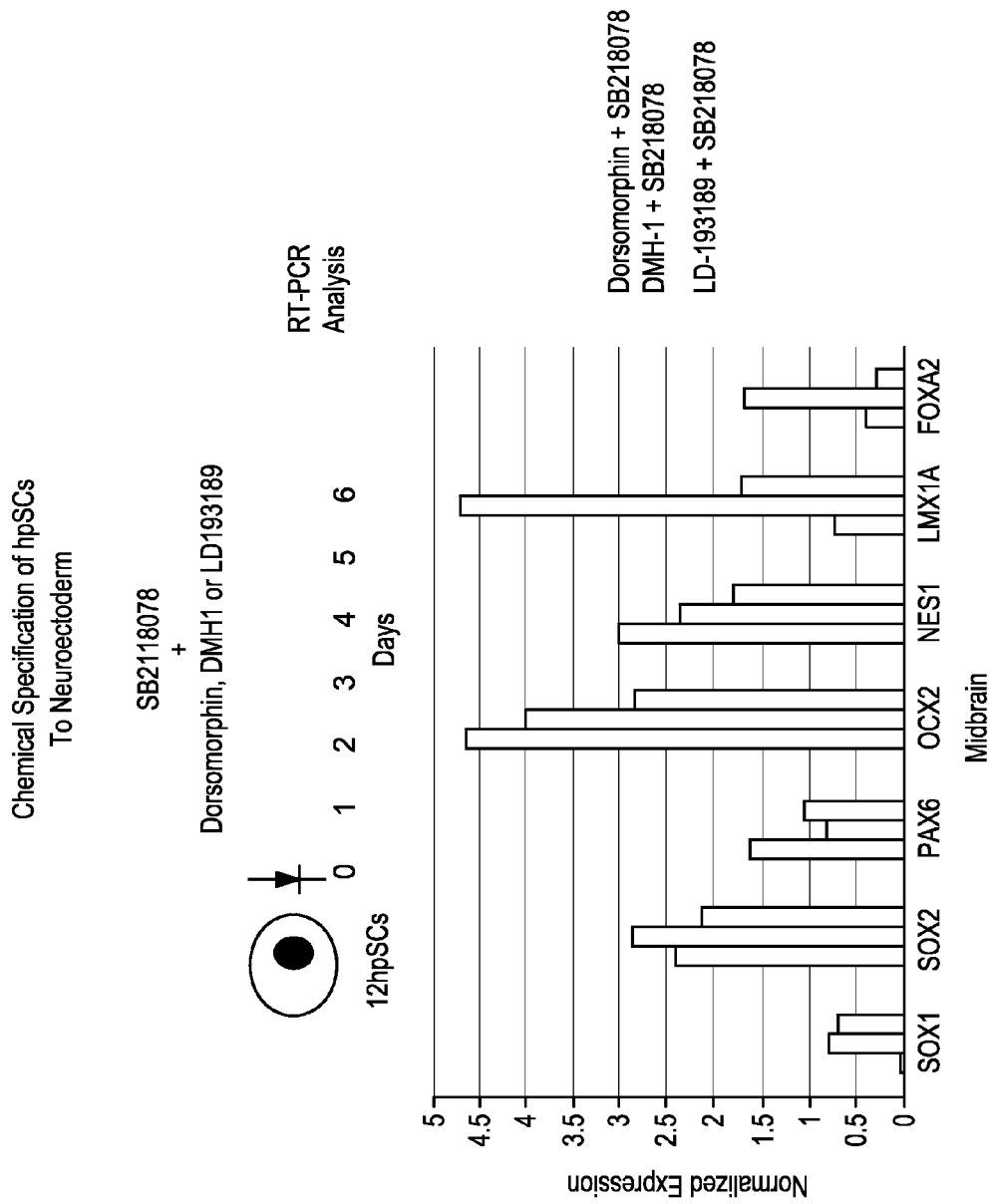
FIG. 3 is a graph showing the expression of Sox1, Sox2, Pax6, Otx2, Lmx1 and Fox2A by RT-PCR on hPSCs treated with SB218078 and Dorsomorphin, DMH-1 or LD193189.
Figure 4:
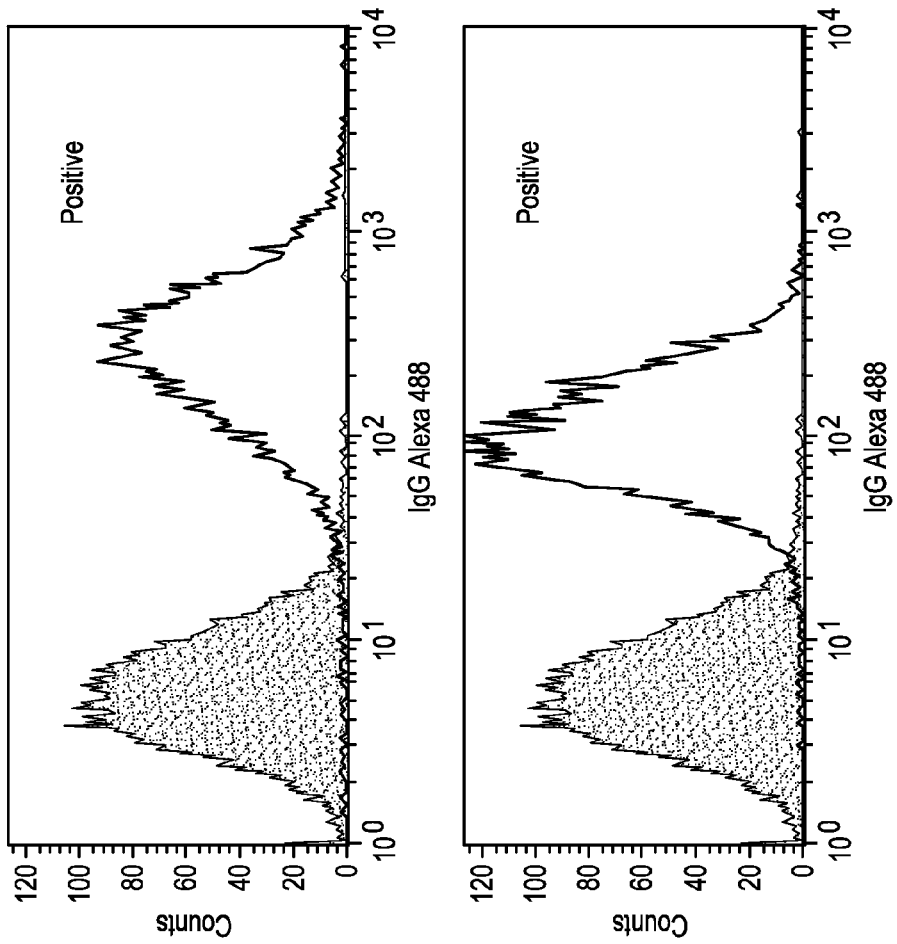
FIG. 4 shows FACs analysis of hPSCs derived NSCs at passage 7 demonstrating expression of Nestin and musashiI.
Figure 5:
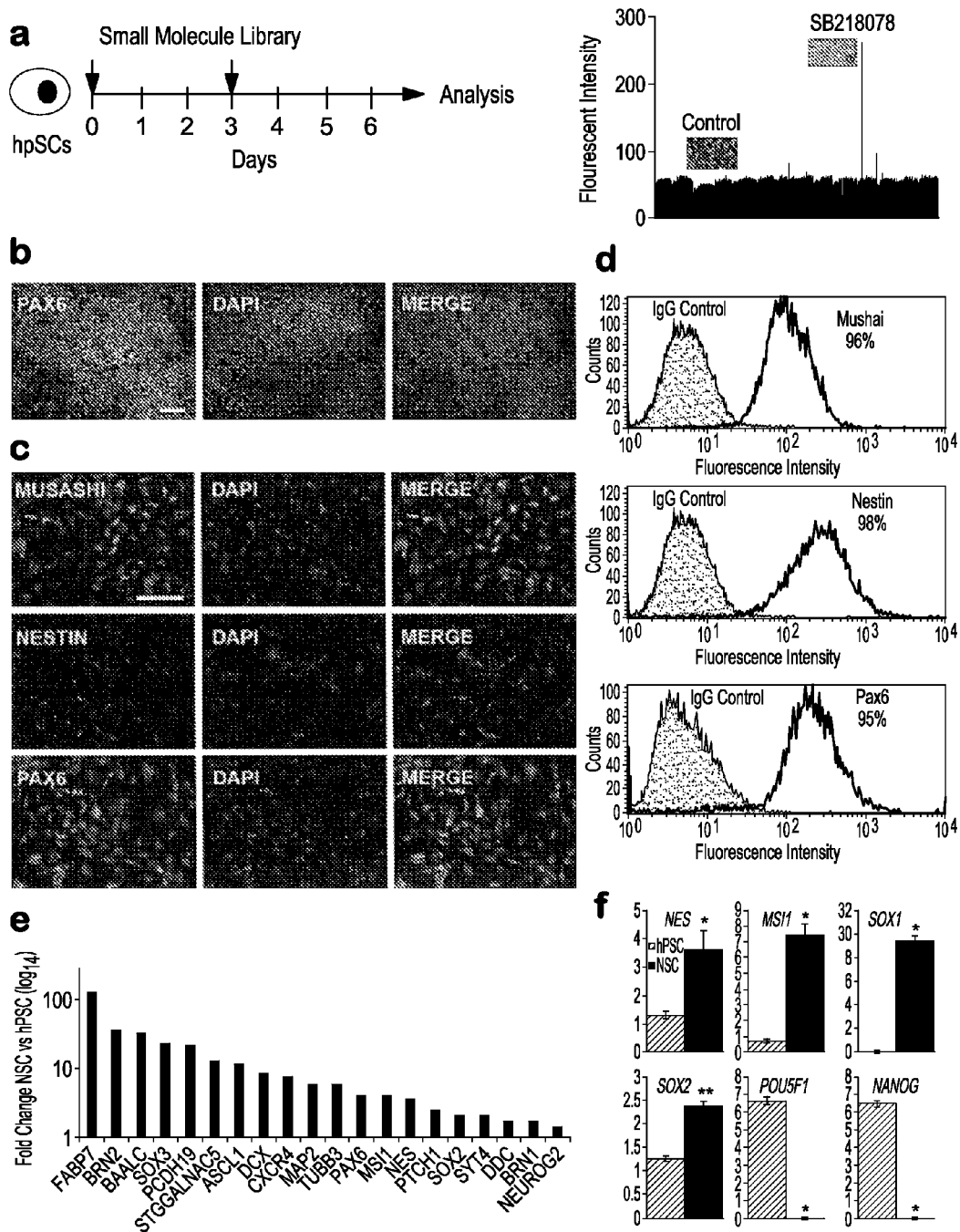
FIG. 5A-F shows the generation of hPSC derived NSCs through small molecules. (A) Diagram showing small molecule screening strategy for the neural induction of hPSCs. (B) hPSCs treated with SB218078 and DMH1 for seven days and stained for PAX6. Scale bar is 100 µm. (C) Expanded hPSC-NSCs stained for Nestin, Musashi, and PAX6. Scale bar is 100 µm. (D) FACS analyses of hPSC-NSC population stained for Musashi, Nestin, PAX6, and OCT4. (E) Gene expression microarray analysis showing fold expression induction of neural markers from hPSCs to NSCs; n=2. (F) Gene expression analysis by RT-PCR of hPSC and hPSC-NSCs. Mean±s.e.m., two-tailed Student's t-test: n=3-5; $\alpha$=0.05; **$P<0.01$;*$P<0.05$.

As shown in the Examples, two potent neural inducers were identified, SB218078 and DMH-1, using a high-throughput screening strategy (FIG. 5A). The hPSC derived NSC (hPSC-NSC) population was positive for Nestin, Musashi-1, PAX6, FABP7, BRN2, SOX3, ST6GALNAC5, CXCR4, DCX, NES, MSI, CD113, CD15, FOXA2, FOXO4, GFAP, LMX1A, MAP2, OTX2, TUBB3, SOX1, SOX2, and ST6GALNAC5 neural stem cell markers and negative for OCT4 and NANOG pluripotency markers (FIGS. 3, 5-B, 5C, 5D and 5F). FABP7 encodes for a brain fatty acid binding protein involved in CNS development and is highly expressed in NSCs. ST6GALNAC5 encodes for alpha 2,6-sialyltransferase, which mediates the passage of cells through the blood brain barrier. Further, NSCs which were derived using SB218078 and DMH-1 expressed LMX1A and FOX2A. LMX1A and FOX2A are expressed on ventral midbrain neuroectodermal cells which are precursors to dopaminergic neurons. These NSCs are suitable for further expansion, cryopreservation and differentiation, making them a practical source for DA neurons. As such, the present invention demonstrates the disclosed methods produced NSCs from hPSCs.

The present invention also provides for the generation of dopaminergic neurons from hPSCs with under defined chemical conditions.

As used herein, "differentiation" refers to a change that occurs in cells to cause those cells to assume certain specialized functions and to lose the ability to change into certain other specialized functional units. Cells capable of differentiation may be any of totipotent, pluripotent or multipotent cells. Differentiation may be partial or complete with respect to mature adult cells.

"Differentiated cell" refers to a non-embryonic cell that possesses a particular differentiated, i.e., non-embryonic, state. The three earliest differentiated cell types are endoderm, mesoderm, and ectoderm.

NSCs derived from hPSCs are multipotent and can be differentiated into several neural cell types including neurons, astrocytes and oligodendrocytes.

Astrocytes, also known collectively as astroglia, are characteristic star-shaped glial cells in the brain and spinal cord. They are the most abundant cell of the human brain. They perform many functions, including biochemical support of endothelial cells that form the blood-brain barrier, provision of nutrients to the nervous tissue, maintenance of extracellular ion balance, and a role in the repair and scarring process of the brain and spinal cord following traumatic injuries.

A neuron is an electrically excitable cell that processes and transmits information through electrical and chemical signals. A chemical signal occurs via a synapse, a specialized connection with other cells. Neurons connect to each other to form neural networks. Neurons are the core components of the nervous system, which includes the brain, spinal cord, and peripheral ganglia. A number of specialized types of neurons exist: sensory neurons respond to touch, sound, light and numerous other stimuli affecting cells of the sensory organs that then send signals to the spinal cord and brain. Motor neurons receive signals from the brain and spinal cord, cause muscle contractions, and affect glands. Interneurons connect neurons to other neurons within the same region of the brain or spinal cord. There are several types of neurons: cholinergic, GABAergic, Glutamatergic, Dopaminergic and Serotonergic.

Cholinergic neurons. Acetylcholine is released from presynaptic neurons into the synaptic cleft. It acts as a ligand for both ligand-gated ion channels and metabotropic (GPCRs) muscarinic receptors. Nicotinic receptors, are pentameric ligand-gated ion channels composed of alpha and beta subunits that bind nicotine. Ligand binding opens the channel causing influx of $Na^+$ depolarization and increases the probability of presynaptic neurotransmitter release.

GABAergic neurons—gamma aminobutyric acid. GABA is one of two neuroinhibitors in the CNS, the other being Glycine. GABA has a homologous function to ACh, gating anion channels that allow $Cl^-$ ions to enter the post synaptic neuron. $Cl^-$ causes hyperpolarization within the neuron, decreasing the probability of an action potential firing as the voltage becomes more negative (recall that for an action potential to fire, a positive voltage threshold must be reached).

Glutamatergic neurons. Glutamate is one of two primary excitatory amino acids, the other being Aspartate. Glutamate receptors are one of four categories, three of which are ligand-gated ion channels and one of which is a G-protein coupled receptor (often referred to as GPCR). AMPA and Kainate receptors both function as cation channels permeable to Na+ cation channels mediating fast excitatory synaptic transmission. NMDA receptors are another cation channel that is more permeable to $Ca^{2+}$. The function of NMDA receptors is dependent on Glycine receptor binding as a co-agonist within the channel pore. NMDA receptors do not function without both ligands present. Metabotropic receptors, GPCRs modulate synaptic transmission and postsynaptic excitability. Glutamate can cause excitotoxicity when blood flow to the brain is interrupted, resulting in brain damage. When blood flow is suppressed, glutamate is released from presynaptic neurons causing NMDA and AMPA receptor activation more so than would normally be the case outside of stress conditions, leading to elevated $Ca^{2+}$ and $Na^+$ entering the post synaptic neuron and cell damage.

Dopaminergic neurons. Dopamine is a neurotransmitter that acts on D1 type (D1 and D5) Gs coupled receptors, which increase cAMP and PKA, and D2 type (D2, D3, and D4) receptors, which activate Gi-coupled receptors that decrease cAMP and PKA. Dopamine is connected to mood and behavior, and modulates both pre and post synaptic neurotransmission. Loss of dopamine neurons in the substantia nigra has been linked to Parkinson's disease.

Serotonergic neurons. Serotonin, (5-Hydroxytryptamine, 5-HT), can act as excitatory or inhibitory. Of the four 5-HT receptor classes, three are GPCR and one is ligand gated cation channel. Serotonin is synthesized from tryptophan by tryptophan hydroxylase, and then further by aromatic acid decarboxylase. A lack of 5-HT at postsynaptic neurons has been linked to depression. Drugs that block the presynaptic serotonin transporter are used for treatment, such as Prozac and Zoloft.

Oligodendrocytes are another type of brain cell. The main function of oligodendrocytes is to provide support and to insulate the axons (the long projection of nerve cells) in the central nervous system (the brain and spinal cord) of some vertebrates. Oligodendrocytes do this by creating the myelin sheath, which is 80% lipid and 20% protein. A single oligodendrocyte can extend its processes to 50 axons, wrapping approximately 1 μm of myelin sheath around each axon. Each oligodendrocyte forms one segment of myelin for several adjacent axons.

Under the proper culture conditions, a subject NSC can be induced to express specific neural genes, such as for example, genes of the mid-brain dopaminergic lineage, e.g., Nurr1 and Pitx3.

A subject NSC can be induced to differentiate into tyrosine hydroxylase (TH)-expressing neurons. TH is a known marker for dopaminergic neurons. In some embodiments, a subject NSC is differentiated into a motor neuron, where the motor neuron is positive for HB9. In some embodiments, a subject NSC is differentiated into a GABAergic neuron, where the GABAergic neuron is positive for GAD67. In some embodiments, a subject induced NSC is differentiated into a dopaminergic neuron, where the dopaminergic neuron is TH positive.

Neurons may be identified by expression of neuronal markers Tuj1 (beta-III-tubulin); MAP-2 (microtubule associated protein 2, other MAP genes such as MAP-1 or -5 may also be used); anti-axonal growth clones; ChAT (choline acetyltransferase); CgA (anti-chromagranin A); DARRP (dopamine and cAMP-regulated phosphoprotein); DAT (dopamine transporter); GAD (glutamic acid decarboxylase); GAP (growth associated protein); anti-HuC protein; anti-HuD protein; .alpha.-internexin; NeuN (neuron-specific nuclear protein); NF (neurofilament); NGF (nerve growth factor); .gamma.-SE (neuron specific enolase); peripherin; PH8; PGP (protein gene product); SERT (serotonin transporter); synapsin; Tau (neurofibrillary tangle protein); anti-Thy-1; TRK (tyrosine kinase receptor); TRH (tryptophan hydroxylase); anti-TUC protein; TH (tyrosine hydroxylase); VRL (vanilloid receptor like protein); VGAT (vesicular GABA transporter), VGLUT (vesicular glutamate transporter).

A neuron generated by inducing differentiation of a subject NSC can be tested according to functional criteria. For example, calcium flux can be measured by any standard technique, in response to a neurotransmitter, or other environmental condition known to affect neurons in vivo. First, neuron-like cells in the population are identified by morphological criteria, or by a marker such as NCAM. The neurotransmitter or condition is then applied to the cell, and the response is monitored. The cells can also be subjected to standard patch-clamp techniques, to determine whether there is evidence for an action potential, and what the lag time is between applied potential and response. Differentiation of a subject NSC can generate cultures that contain subpopulations that have morphological characteristics of neurons, are NCAM or MAP-2 positive, and show a response to one or more of GABA, acetylcholine, ATP, and high sodium concentration, glutamate, glycine, ascorbic acid, dopamine, or norepinephrine. In some embodiments, a subject differentiated NCAM or MAP-2 positive can also exhibit an action potential in a patch-clamp system.

Markers for dopaminergic neurons include, but are not limited to, TUJ1, TH, Dat, Foxa2, Nurr-1, Girk2, MAPT, SYT4, FOXA1, DDC, ASCL1, PINK1, PAX5, LMX1B, PITX3, NURR-1, LMX1A, EN1, PAX2, TFF3, PITX2, DCX, MAP2, PITX1 or VMAT2, or any combination thereof.

Astrocytes can be identified by expression of astrocyte markers GFAP (glial fibrillary acidic protein); S100.beta.; and the like.

Oligodendrocytes can be generated from a subject induced NSC. Oligodendrocytes may be identified by expression of oligodendrocyte markers GC (galactocerebroside, also referred to as GalC); MBP (myelin basic protein); CNPase (2',3'-cyclic nucleotide 3'-phosphodiesterase [or -phosphohydrolase]); or the oligodendrocyte markers neuroendocrine-specific protein-4 (NSP4; also known as reticulon-4 or RTN4), RIP (2',3'-cyclic nucleotide 3'-phosphodiesterase), myelin/oligodendrocyte specific protein (MOSP), oligodendrocyte lineage transcription factor 2 (Olig2), oligodendrocyte marker O1, NogoA, or oligodendrocyte marker O4.

The present invention provides a high-throughput screening assay for DA neuron differentiation from NSCs.

In another embodiment, the present invention provides a method to generate dopaminergic neurons. The method includes treating human pluripotent stem cells (hPSCs) with a checkpoint kinase 1 (CK1) inhibitor and a bone morphogenic protein (BMP) inhibitor, identifying neural stem cells by assaying the treated hPSCs for neural stem cell markers, treating NSCs with at least one dopaminergic neuron inducing compound and analyzing cells for dopaminergic neuron cell markers. In certain aspects, the CK1 inhibitor is SB218078 and the BMP inhibitor is Dorsomorphin, LD-193189 or DMH-1. In a preferred aspect, the CK1 inhibitor is SB218078 and the BMP inhibitor is DMH-1.

In an aspect, the hPSCs are human embryonic stem cells (hESCs), human parthenogenetic stem cells (hpSCs) or induced pluripotent stem cells (iPSCs), or cell lines derived therefrom.

In one aspect of the method, the neural stem cell markers maybe BRN2, CD113, CD15, CXCR4, DCX, FABP7, FOXA2, FOXO4, GFAP, LMX1A, Musashi-1, MAP2, Nestin, OTX2, PAX6, TUBB3, SOX1, SOX2, SOX3 or ST6GALNAC5, or any combination thereof.

In a further aspect of the method, the dopaminergic neuron inducing compound maybe Homoquinolinic acid, L-Cysteinesulfinic acid, Kynurenic acid, (R)-(+)-HA-966, m-Chlorophenylbiguanide hydrochloride, Calpeptin, Dimaprit dihydrochloride, 8-Hydroxy-DPAT hydrobromide, trans-4-Hydroxycrotonic acid, Fasudil hydrochloride, Thioperamide, Retinoic acid, AM580, TTNPB, Remoxipride hydrochloride, ICI 215,001 hydrochloride, Imiloxan hydrochloride, Spiperone hydrochloride, Kenpaullone, CL 218872, CV 1808, Ro 15-4513, Linopirdine dihydrochloride, Guggulsterone, Ch 55, 3-MATIDA, SEW 2871, Immethridine dihydrobromide, LY 364947, Tranylcypromine hydrochloride, (−)-Cytisine or Nilutamide, or any combination thereof. In a preferred aspect, the dopaminergic neuron inducing compound is Guggulsterone.

In an additional aspect of the method, the dopaminergic neuron cell markers maybe TUJ1, TH, Dat, Foxa2, Nurr-1, Girk2, MAPT, SYT4, FOXA1, DDC, ASCL1, PINK1, PAX5, LMX1B, PITX3, NURR-1, LMX1A, EN1, PAX2, TFF3, PITX2, DCX, MAP2, PITX1 or VMAT2, or any combination thereof.

In a further embodiment, the present invention provides for dopaminergic neurons. The subject DA neurons are generated by treating human pluripotent stem cells (hPSCs) with a checkpoint kinase 1 (CK1) inhibitor and a bone morphogenic protein (BMP) inhibitor, identifying neural stem cells by assaying the treated hPSCs for neural stem cell markers, treating NSCs with at least one dopaminergic neuron inducing compound and analyzing cells for dopaminergic neuron cell markers. In certain aspects, the CK1 inhibitor is SB218078 and the BMP inhibitor is Dorsomorphin, LD-193189 or DMH-1. In a preferred aspect, the CK1 inhibitor is SB218078 and the BMP inhibitor is DMH-1.

In an aspect, the hPSCs are human embryonic stem cells (hESCs), human parthenogenetic stem cells (hpSCs) or induced pluripotent stem cells (iPSCs), or cell lines derived therefrom.

In one aspect of the method, the neural stem cell markers maybe BRN2, CD113, CD15, CXCR4, DCX, FABP7, FOXA2, FOXO4, GFAP, LMX1A, Musashi-1, MAP2, Nestin, OTX2, PAX6, TUBB3, SOX1, SOX2, SOX3 or ST6GALNAC5, or any combination thereof.

In a further aspect of the method, the dopaminergic neuron inducing compound maybe Homoquinolinic acid, L-Cysteinesulfinic acid, Kynurenic acid, (R)-(+)-HA-966, m-Chlorophenylbiguanide hydrochloride, Calpeptin, Dimaprit dihydrochloride, 8-Hydroxy-DPAT hydrobromide, trans-4-Hydroxycrotonic acid, Fasudil hydrochloride, Thioperamide, Retinoic acid, AM580, TTNPB, Remoxipride hydrochloride, ICI 215,001 hydrochloride, Imiloxan hydrochloride, Spiperone hydrochloride, Kenpaullone, CL 218872, CV 1808, Ro 15-4513, Linopirdine dihydrochloride, Guggulsterone, Ch 55, 3-MATIDA, SEW 2871, Immethridine dihydrobromide, LY 364947, Tranylcypromine hydrochloride, (−)-Cytisine or Nilutamide, or any combination thereof. In a preferred aspect, the dopaminergic neuron inducing compound is Guggulsterone.

In an additional aspect of the method, the dopaminergic neuron cell markers maybe TUJ1, TH, Dat, Foxa2, Nurr-1, Girk2, MAPT, SYT4, FOXA1, DDC, ASCL1, PINK1, PAX5, LMX1B, PITX3, NURR-1, LMX1A, EN1, PAX2, TFF3, PITX2, DCX, MAP2, PITX1 or VMAT2, or any combination thereof.

Figure 6:
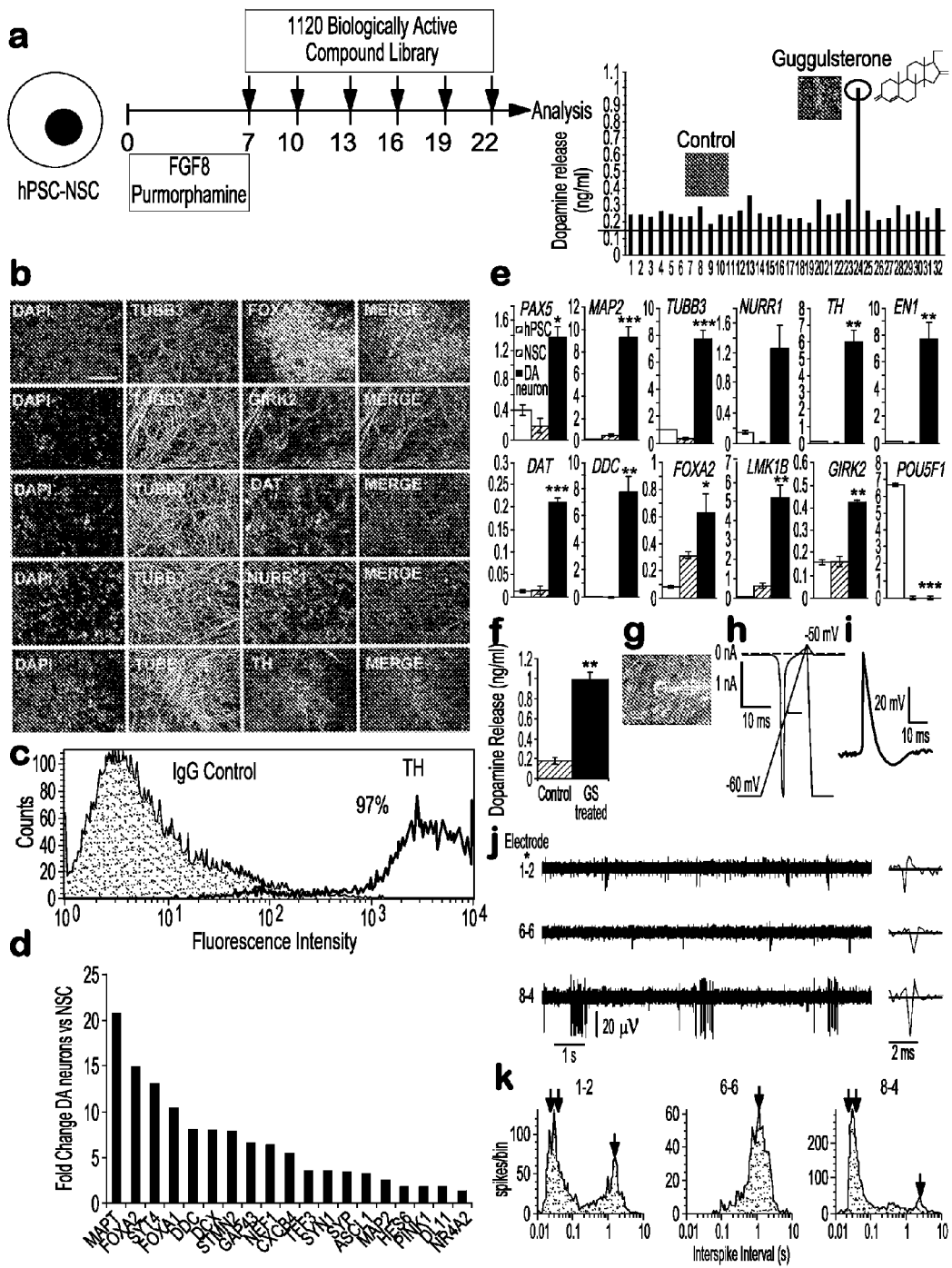
FIG. 6A-K shows that Guggulsterone promotes generation of DA neurons. (A) Diagram showing small molecule screening strategy for the differentiation of hPSC derived NSCs (hPSC-NSC) into DA neurons. (B) Staining for dopaminergic markers after 30 days of guggulsterone (GS) treatment. Scale bar is 100 µm. (C) FACS analysis of derived DA neurons stained for TH. (D) Fold induction of dopaminergic markers from NSCs to DA neurons as determined by gene expression microarray analysis; n=2 (E) Relative gene expression by RT-PCR in DA neurons, NSCs and undifferentiated hPSCs. Mean±s.e.m., one-factor ANOVA with Dunnett test comparing expression of DA neurons and NSCs against hPSC controls: n=3-5; $\alpha$=0.05; *$P<0.001$; $P<0.01$; *$P<0.05$. (F) Dopamine release assay of GS-treated neurons versus control cells (NSCs treated for 1 week with 100 ng/ml FGF8 and 2 µM purmorphamine and 2 weeks with 0.1% DMSO instead of GS). Mean±s.e.m., two-tailed Student's t-test: n=3; $\alpha$=0.05; **$P<0.01$. (G) Representative phase-contrast image of a whole-cell patch-clamped GS-treated neuron. Scale bar is 10 µm. (H) Sodium current elicited with application of voltage ramp from −60 to +50 mV to cell in (G) in voltage clamp mode. Ramp parameters and waveform are shown in red superimposed on the current trace. The blue arrow indicates the point at which the stimulation ramp crossed the 0 mV value. (I) Action potential elicited from cell in (g) by injection of 500 pA for 200 ms in current clamp mode. Action potentials were found in 7 out of 20 cells patch-clamped. (J) Extracellular microelectrode array (MEA) recordings of GS-treated neurons, showing 10 s voltage traces for three representative electrodes. A single spike for each electrode is expanded at right. (K) Interspike interval histograms for electrodes in (j) showing: (↓↓) peaks associated with intervals between spikes within a burst and; (↓) those for longer intervals between bursts, or between individual spikes on non-bursting electrodes. Recordings were performed in duplicate.

As shown in the Examples, the disclosed methods resulted in the production of fully functional dopaminergic neurons. The DA neurons displayed neurite outgrowth and for dopamine release (FIG. 6A). Guggulsterone (GS) was identified as one of the best inducers of dopaminergic differentiation (FIG. 6A). The GS-treated cells displayed neurite extensions and expressed TUJ1, TH, Dat, Foxa2, Nurr-1, and Girk2 (FIG. 6B), MAPT, FOXA2, SYT4, FOXA1, DDC, ASCL1, PINK1, PAX5, LMX1B, PITX3, NURR1, LMX1A, EN1, GIRK2, DDC, and VMAT2 (FIGS. 6B, 6D and 6E). Furthermore, FACS analysis revealed that more than 97% of the cells gated were TH positive (FIG. 6C). SYT4 (Synaptotagmin 4) plays an important role in synaptic plasticity and dopamine release. ASCL1 is expressed in the ventral mesencephalon and indicates the derived cells are of the appropriate phenotype. Whole cell patch-clamp electrophysiology (FIG. 6G, FIG. 6H, and FIG. 6I) revealed that the DA neurons displayed inward Na+ current in voltage-clamp mode (FIG. 6H), and fired action potentials when current was injected in the current-clamp mode (FIG. 6I). This demonstrates the production of fully functional dopaminergic neurons from hPSCs using the disclosed methods.

NSCs may play a vital role in the treatment of neurological diseases and disorders. Neurodegeneration is the umbrella term for the progressive loss of structure or function of neurons, including death of neurons. Many neurodegenerative diseases including Parkinson's, Alzheimer's, and Huntington's occur as a result of neurodegenerative processes and are characterized by progressive nervous system dysfunction. Neurological diseases and disorders include but are not limited to, Alzheimer's Disease and other dementias, Brain Cancer, Degenerative Nerve Diseases, Encephalitis, Epilepsy, Genetic Brain Disorders, Head and Brain Malformations, Hydrocephalus, Stroke, Parkinson's Disease, Multiple Sclerosis, Amyotrophic Lateral Sclerosis (ALS or Lou Gehrig's Disease), Huntington's Disease, Prion Diseases, stroke and others.

Neural stem cells have been shown to engage in migration and replacement of dying neurons. Additionally, the role of hippocampal stem cells during stroke in mice has been elucidated. These results demonstrated that NSCs can engage in the adult brain as a result of injury. Furthermore, if has been demonstrated that NSCs migrate to brain tumors in a directed fashion. Further, molecular mechanism for the responses of NSCs to injury has been investigated. Chemokines released during injury, such as SDF-1a, were responsible for the directed migration of human and mouse NSCs to areas of injury in mice. The search for additional mechanisms that operate in the injury environment and how they influence the responses of NSCs during acute and chronic disease is matter of intense research.

In an additional embodiment, the present invention provides a method of treatment for neurological diseases and disorders. The method includes the administration of NSCs to a subject with a neurological disease or disorder.

In a further embodiment, the present invention provides a method of treating neurological diseases and disorders. The method includes the administration of NSCs or DA neurons to a subject with a neurological disease or disorder.

In another embodiment, the present invention provides a kit for the production of NSCs. The kit may include a checkpoint kinase 1 (CK1) inhibitor and a bone morphogenic protein (BMP) inhibitor, reagents to identify neural stem cell markers and directions for the generation of NSCs from hPSCs. In one aspect, the CK1 inhibitor is SB218078 and the BMP inhibitor is Dorsomorphin, LD-193189 or DMH-1. In certain aspects the CK1 inhibitor is SB218078 and the BMP inhibitor is Dorsomorphin; CK1 inhibitor is SB218078 and the BMP inhibitor is LD-193189; CK1 inhibitor is SB218078 and the BMP is DMH-1. The kit may include reagents to identify BRN2, CD113, CD15, CXCR4, DCX, FABP7, FOXA2, FOXO4, GFAP, LMX1A, Musashi-1, MAP2, Nestin, OTX2, PAX6, TUBB3, SOX1, SOX2, SOX3 or ST6GALNAC5 neural stem cell markers.

In another embodiment, the present invention provides a kit for the production of dopaminergic neurons. The kit includes a checkpoint kinase 1 (CK1) inhibitor and a bone morphogenic protein (BMP) inhibitor, reagents to identify neural stem cell markers, at least one dopaminergic neuron inducing compound, reagents to identify dopaminergic neuron cell markers and directions for the production of dopaminergic neurons from hPSCs. In one aspect, the CK1 inhibitor is SB218078, the BMP inhibitor is DMH-1 and the dopaminergic neuron inducing compound is Gugglesterone. The kit may include reagents to identify BRN2, CD113, CD15, CXCR4, DCX, FABP7, FOXA2, FOXO4, GFAP, LMX1A, Musashi-1, MAP2, Nestin, OTX2, PAX6, TUBB3, SOX1, SOX2, SOX3 or ST6GALNAC5 neural stem cell markers. The kit may also include reagents to identify TUJ1, TH, Dat, Foxa2, Nurr-1, Girk2, MAPT, SYT4, FOXA1, DDC, ASCL1, PINK1, PAX5, LMX1B, PITX3, NURR-1, LMX1A, EN1, PAX2, TFF3, PITX2, DCX, MAP2, PITX1 or VMAT2 dopaminergic neuron cell markers.

The following examples are intended to illustrate, but not limit the invention.

Example 1

Growth of hPSCs

Two potent neural inducers were identified, SB218078 and DMH-1, using a high-throughput screening strategy (FIG. 5A). SB218078 is a structural homolog of stauprimide, which has been shown to prime embryonic stem cells for differentiation, and DMH-1 is a homolog of dorsomorphin, which efficiently induces neural conversion in hPSCs. To derive NSC, primitive neuroepithelium was induced by switching the hPSCs grown on Matrigel from StemPro to N2B27 medium supplemented with 5 µM SB218078 and 1 µM DMH-1. After 6 days in the presence of these neural inducers, Pax6, an early marker of neural induction, was significantly up-regulated (FIGS. 3 and 5B). On day 7, the neuralized hPSCs were switched to NSC medium and then dissociated to derive proliferative NSCs. After 4 passages, the hPSC derived NSC (hPSC-NSC) population was 98% positive for Nestin, 96% for Musashi-1, 95% for PAX6, 0% for OCT4 (FIG. 5C and FIG. 5D). Gene expression microarray analysis revealed up-regulation of putative NSC markers including FABP7, BRN2, SOX3, ST6GALNAC5, CXCR4, DCX, NES, and MSI (FIG. 5E). FABP7 encodes for a brain fatty acid binding protein involved in CNS development and is highly expressed in NSCs. ST6GALNAC5 encodes for alpha 2,6-sialyltransferase, which mediates the passage of cells through the blood brain barrier. Real-time PCR (RT-PCR) data further confirmed the up-regulation of NSC markers and, most importantly, revealed the complete down-regulation of the pluripotency markers OCT-4 and NANOG (FIG. 5F), leading to the conclusion that a highly enriched population of neural stem cells had been obtained. These NSCs are suitable for further expansion, cryopreservation and differentiation, making them a practical source for DA neurons.

Specifically, the hPSC lines [human embryonic stem cell line WA-09 and human parthenogenetic stem cell lines LLC2P and LLC12PH (International Stem Cell Corporation) were first maintained on a mitomycin-C inactivated mouse embryonic fibroblast (Millipore) feeder layer in embryonic stem cell medium: Knock Out DMEM/F12 (Life Technologies), 2 mM L-glutamine (GlutaMax-I, Invitrogen), 0.1 mM MEM nonessential amino acids (Life Technology), 0.1 mM β-mercaptoethanol (Life Technologies), penicillin/streptomycin/amphotericin B (100 U/100 µg/250 ng) (MP Biomedicals) and 5 ng/ml bFGF (Peprotech). Cells were passaged with dispase (Life Technologies) every 5-7 days with split ratio of 1:4 or 1:6. The hPSCs were then transferred to Matrigel (BD Biosciences) coated plates and grown with Stem Pro hESC SFM medium (Invitrogen): DMEM/F12 with GlutaMAX, 1× STEMPRO hESC SFM Growth Supplement, 1.8% Bovine Serum Albumin, 8 ng/mL bFGF and 0.1 mM 2-Mercaptoethanol.

Example 2

Feeder Free Growth of hPSCs

The hPSC line LLC12PH were then transferred to Matrigel (BD Biosciences) coated plates and grown with Stem Pro hESC SFM medium (Invitrogen): DMEM/F12 with GlutaMAX, 1× STEMPRO hESC SFM Growth Supplement, 1.8% Bovine Serum Albumin, 8 ng/mL bFGF and 0.1 mM 2-Mercaptoethanol.

Example 3

High-Throughput Neuroindeuction hPSCs Screening Assay hPSC-NSCs were derived by treating undifferentiated hPSCs growing under feeder-free culture conditions with a chemical combination consisting of SB218078 (5 µM) plus DMH-1 (1 µM) in N2B27 Medium [Knockout DMEM/F12, 1× GlutaMax, 1×N2/B27 Supplement (Invitrogen)] for 7 days. The neuralized hPSCs were then dissociated with Accutase (Sigma) and grown on Matrigel coated plates in NSC medium [KnockOut DMEM/F12, 2% StemPro Neural Supplement, 1× GlutaMAX, 20 ng/ml bFGF and 20 ng/ml EGF] for ≥4 passages to generate and highly pure and homogeneous population of hPSC-NSCs.

Example 4

High-Throughput Dopamine Neuron Cell Differentiation Screening Assay

To obtain DA neurons, hPSC-NSC were first primed into DA precursors with 100 ng/mL FGF8 and 2 µM Purmorphamine for 7 days and then used to screen for small molecules that induce terminal dopaminergic differentiation (FIG. 6A). The DA precursors were plated at 2000 cells/well of a 96-well plate and treated with a small molecule library (Tocris 1120 biologically active compounds) at 2.5 µM for two weeks (FIG. 6A). Dopaminergic differentiation was assessed by neurite outgrowth and ELISA analysis for dopamine release (FIG. 6A). From this screen, guggulsterone (GS), a naturally occurring steroid, was identified among the best inducers of dopaminergic differentiation (FIG. 6A). After 30 days of differentiation, GS-treated neurons appeared mature with elaborate neurite extensions. At this stage, the derived cells expressed not only the major neuronal marker β-III-tubulin (TUJ1), but also the important DA neuron markers tyrosine hydroxylase (TH), the dopamine transporter (Dat), Foxa2, Nurr-1, and Girk2 (FIG. 6B). Furthermore, FACS analysis revealed that more than 97% of the cells gated were TH positive (FIG. 6C). Gene expression microarray analysis indicated up-regulation of dopaminergic and neuronal associated markers such as MAPT, FOXA2, SYT4, FOXA1, DDC, ASCL1, and PINK1 (FIG. 6D). SYT4 (Synaptotagmin 4) plays an important role in synaptic plasticity and dopamine release. ASCL1 is expressed in the ventral mesencephalon and indicates the derived cells are of the appropriate phenotype. Further analysis of the gene expression of hPSC, NSC, DA neurons, and tissue from the substantia nigra revealed that the hPSC-derived DA neurons have acquired elements of the gene expression signature characteristic of cells undergoing neural differentiation toward cells present in the SN, and that they are developmentally located after the NSC and before the SN stage. RT-PCR further confirmed the DA neuron identity with the characteristic expression of markers such as PAX5, LMX1B, PITX3, NURR1, LMX1A, EN1, GIRK2, DDC, and VMAT2 (FIG. 6E). Most importantly, compared to control cells (NSCs treated for 1 week with FGF8 and purmorphamine and 2 weeks with 0.1% DMSO instead of GS), GS-treated cells demonstrated a five-fold increase in dopamine secretion as determined by ELISA (FIG. 6F). Whole cell patch-clamp electrophysiology (FIG. 6G, FIG. 6H, and FIG. 6I) revealed that after 90 days of GS treatment, the DA neurons displayed inward Na+ current in voltage-clamp mode (FIG. 6H), and fired action potentials when current was injected in the current-clamp mode (FIG. 6I). Spontaneous action potentials were recorded in whole cultures of GS-treated neurons using a microelectrode array (MEA) system (FIG. 6J). Approximately one third of the 64 total electrodes in MEA dishes showed moderate activity (>5 spikes/min). These neurons are characterized by two basic firing phenotypes: those that fire periodic bursts of spikes, and those that regularly fire single spikes (FIG. 6J and FIG. 6K).

The method specifically involved treating both hESC-H9-NSCs (Invitrogen) and hPSC-NSCs with Purmorphamine (2 µM) and FGF8 (100 ng/mL) in NB medium [NeuroBasal medium, 1× GlutaMAX, 1× N2/B27 Supplement (Invitrogen)] for 7 days. After 7 days of Purmorphamine and FGF8 treatment, the NSCs were dissociated with Accutase (Sigma) and plated 20,000 cells/mL into Matrigel coated 96 well plates and treated with small molecule library (Torcris 1120 Biologically Active Compounds) at 2.5 µM final concentration for two weeks (FIG. 6A). Two weeks after treatment with small molecules, all wells were visually observed and scored based on neurite density. Two weeks after treatment with small molecules, all wells were visually observed and scored based on neurite density and dopamine release. For measuring neurite density, cells were fixed with 4% paraformaldehyde and phase contrast images were acquired using Cellavista Cell Imaging System (Roche Applied Science) from randomly selected fields. Neurite density was measured using the Cellavista density software image processing program. Each experimental condition was done in duplicate wells, and at least three independent experiments were conducted to acquire the final results.

Conditioned medium from the top neurite inducers (Table 1) (wells containing the highest density of neurites compare to control 0.1% DMSO treated) were collected and analyzed using a dopamine ELISA assay (Cosmo Bio). Conditioned medium was collected from samples containing 50,000 cells per well and centrifuged at 3000 RPM to remove cell debris. Supernatant was then collected and analyzed for quantitative determination of dopamine using a commercial dopamine ELISA assay kit (CusaCosmo Bio). Data analysis was performed using the microtiter plate reader (BIO-TEK Synergy 2). The results presented are from three independent experiments (n=3) and represented as mean±standard error of mean (s.e.m.) and statistical analysis was performed using the two-tailed Student's t-test with a confidence level of 95% ($\alpha$=0.05) with statistical significance of P<0.05. Additionally, total RNA from each well were collected and analyze by RT-PCR for expression of TuJ1, MAP2, TH, GRK2, EN1, DAT, AADC, PAX2, NURR1, PITX3 and LMX1B from hPSC-NSCs (Table 2). Analysis of the RT-PCR data indicated that all of the best hits express the genes associated with mature dopamine neurons after two week of treatment. Analysis of the ELISA data indicated the top small molecule neurite inducers produced higher levels of dopamine than control non-treated cells (1.5 ng/mL). Guggulsterone treated hPSC-NSCs induced the highest levels of Dopamine spontaneous release (FIG. 5A). The percentages of TH positive cells produced by chemical treatment with Kenpaullone (33%), Guggulsterone (35%), Kynurenic Acid (19%), Immedthridine Dihydrobromide (21%), and Dimaprit Dihydrochloride (18%) were higher than 15% of TH positive cells obtained from hPSC-NSCs differentiated for ≥1 month using a standard dopaminergic differentiation medium (BDNF 20 ng/mL, GDNF 20 ng/mL, cAMP 200 µM, Abscorbic Acid 200 µM, TGFβ3 2 ng/mL and DAPT).

Whole cell patch clamp electrophysiology methods. For electrophysiological recordings, the cells were transferred to a recording chamber mounted on an inverted Olympus microscope. During the recordings the temperature was maintained at 31-32° C., and the cells perfused at constant flow of 1 ml/min. with 150 mM NaCl, 4 mM KCl, 1.8 mM $CaCl_2$, 1 mM $MgCl_2$, 10 mM HEPES, 10 mM Glucose at pH 7.30 and 315 mOsm. Whole-cell recordings were obtained using borosilicate electrodes with tip resistance of 2-3 MΩ, filled with 130 mM K-Gluconate, 5 mM NaCl, 5 mM KCl, 10 mM HEPES, 20 mM Sucrose, 0.3 mM EGTA, 3 mM MgATP at pH 7.30 and 290 mOsm. Data were acquired using an HEKA EPC-10 digitizer/amplifier. Once whole-cell access was achieved the resting membrane potential was immediately recorded; the cells were then allowed to equilibrate for 3-5 min. From a resting membrane potential of −70 mV, the cells were then depolarized in current-clamp mode with 200 ms current injections, delivered at 0.2 Hz., and with increasing amplitude from 50 pA to up to 1000 pA to induce action potentials. The presence of inward or outward currents was determined by applying a voltage ramp. Cells with unstable recording configuration or for which the series resistance became larger than 15MΩ were excluded from the study. Twenty different cells were recorded and action potentials were obtained from 7 patch-clamped cells.

Microarray analysis methods. Total RNA was extracted from collected from duplicate sample pellets (RNeasy; Qiagen) according to the manufacturer's protocol. RNA quantity (Qubit RNA BR Assay Kits; Invitrogen) and quality (RNA6000 Nano Kit; Agilent) was determined to be optimal for each sample before further processing. 200 ng RNA per sample was amplified using the Illumina Total Prep RNA Amplification Kit according to manufacturer's protocol and quantified as above. 750 ng biotinylated RNA per sample was hybridized to Illumina HT-12v4 Expression BeadChips, scanned with an Illumina iScan Bead Array Scanner, and quality controlled in GenomeStudio and the lumi bioconductor package. All RNA processing and microarray hybridizations were performed according to manufacturer's protocols. In GenomeStudio, probes were filtered for those detected with a P value of 0.01 in at least one sample and exported for normalization in R. Raw probe expression values were transformed and normalized using the robust spline normalization (RSN) as implemented in the lumi R/Bioconductor package. To obtain the Venn Diagram, Qlucore Omni Explorer was used. Transcripts that were differentially expressed between pairs of cell types (hPSC vs Substantia Nigra, hPSC vs NSC, and hPSC vs Dopaminergic neurons) were identified using two-tailed Student's t-test with P-value cut-off of <0.05 and a variance cut-off of >0.005. The sets of differentially expressed probes were then compared to each other. The gene expression array data is available at the NCBI GEO database under the accession designation GSE42265.

Statistical analysis. The results are presented as mean±standard error of mean (s.e.m.) and statistical analysis was performed using a confidence level of 95% ($\alpha=0.05$) with two-tailed Student's t-test for comparing two groups or one factor ANOVA with Dunnett test for comparing multiple groups against control. The criterion for statistical significance for all tests was $P<0.05$.

Additional Methods

RT-PCR Analysis

Total RNA from at least triplicate samples with around 1 million cells each was isolated using either QIAsymphony automatic purification system or RNeasy Plus Mini kit, according to manufacturer's instructions (Qiagen). Total RNA was used for reverse transcription with the iScript cDNA synthesis kit (Biorad) and Px2 Thermal Cycler (Thermo Scientific). To analyze gene expression, PCR reactions were performed in duplicate using ¹/₂₅-th of the cDNA per reaction and the QuantiTect Primer Assay and Quantitest SYBR Green master mix (Qiagen). qPCR was performed using the Rotor-Gene Q (Qiagen) 5 min at 95° C., 5 s at 92° C., and 20 s at 60° C. for 37 cycles followed by melt to check the specificity of the amplicons from 50 to 99° C. raising by 1° C. each step. Relative quantification was performed against a standard curve and quantified values were normalized against the input determined by PPIG. The primers used for the analysis are listed in Supplementary Table S1. The results are presented as presented as mean±s.e.m. and statistical analysis was performed using a confidence level of 95% ($\alpha=0.05$) with the two-tailed Student's t-test for comparing two groups or one-factor ANOVA with Dunnett test for comparing multiple groups against control and $P<0.05$ was considered significant.

Immunocytochemistry

Around 100,000 cells per sample were fixed with 4% paraformaldehyde for 10 min at room temperature, washed with PBS, and permeabilized and blocked for 1 hour at room temperature in 0.3% Triton X-100, 5% normal donkey serum, and 1% BSA in PBS. The cells were incubated overnight at 4° C. with primary antibodies in 0.3% Triton X-100, 2% BSA in PBS. Cells are washed three times with PBS and incubated for 1 hour at room temperature with secondary antibodies in 0.3% Triton X-100, 5% normal donkey serum, and 1% BSA in PBS. The nuclei were stained with DAPI. All antibodies used are listed in Supplementary Table S2. Representative images are shown from at least three independent experiments.

Flow Cytometry

For flow cytometry analysis, 1 million cells per sample were harvested with Accutase, washed with PBS, and fixed with 4% paraformaldehyde for 30 min at room temperature. Cells were washed twice with PBS and blocked for 1 hour at room temperature with 0.3% Triton X-100, 5% normal donkey serum, and 1% BSA in PBS. Cells were then incubated overnight at 4° C. with primary antibody in 0.3% Triton X-100, 5% normal donkey serum, and 1% BSA in PBS. Cells were washed twice with PBS and incubated for 1 hour at room temperature with secondary antibody in 0.3% Triton X-100, 5% normal donkey serum, and 1% BSA in PBS. The samples were run on a Becton Dickinison FACSCalibur™ 4-color flow cytometer and the data was analyzed with CellQuest Pro™ software (v6.0). The antibodies used are listed in Supplementary Table S2. Representative results are shown from three independent experiments.

Microelectrode Array (MEA) System

Extracellular voltage recordings from cultured hPSC-derived DA neurons were made on day 95 of differentiation in NB medium [NeuroBasal medium, 1× GlutaMAX, 1× N2/B27 Supplement (Invitrogen)] supplemented with 2.5 µM guggulsterone at 37° C. using a Muse microelectrode array (MEA) system (Axion Biosystems). The surface of the MEA dishes contained an 8×8 grid (64 electrodes total) of 30 µm diameter round extracellular electrodes composed of nanoporous platinum, with 200 µm inter-polar spacing.

MEA dishes were sterilized by rinsing 3 times in sterile deionized water, once in 70% ethanol and once in 100% ethanol. Dishes were then capped and inverted in a covered petri dish, and baked at 50° C. for 4-5 hr. A polyethyleneimine (PEI) base coating was deposited by adding 500 ml of filtered (0.22 µm filter) 0.1% PEI in sodium borate buffer (15 mM; pH 8.4) to each dish and incubating at room temperature for 1 hr. Immediately following aspiration of the PEI solution, dishes were washed 4× with 1 ml deionized water, and air-dried overnight in a tissue culture hood. 75 µl of a sterile Matrigel solution diluted 1:30 in KnockOut DMEM/F12 was added directly over the electrode grid, and the dish was incubated for 1 hr at 37° C. in a tissue culture incubator. The Matrigel solution was then removed and 50 µl of 2.5 µM guggulsterone in NB media containing approximately 100,000 cells were plated onto the surface of the MEA and incubated at 37° C. for 30 min to allow cell attachment. The DA neurons had been previously cultured on Matrigel in 2.5 µM guggulsterone in NB media for 65 days and were removed from the plate by mechanical trituration. After the 30 min incubation, 550 µl of NB media was added to the MEA well and incubated at 37° C. for 24 hours. Media was exchanged and then every 3-4 days thereafter.

Voltage data were sampled simultaneously on all electrodes at 12.5 kHz with a hardware filter bandwidth of 200-5000 Hz, and saved to computer with AxIS software (Axion Biosystems). To remove high-frequency electrical noise before neuronal spike detection, raw signals were treated in software with a 200-2500 Hz single-order Butterworth band-pass filter. Action potential spikes were identified with a detection threshold set to ±5 times standard deviation of the baseline electrode noise. This threshold generally equaled between 7.5 and 11.25 µV. Color-coded spike rate maps were made with AxIS. For spike raster plots and inter-spike interval histograms, time-stamps of detected spikes were exported to Neuroexplorer (NEX Technologies). Two independent recordings were performed.

TABLE 1

| Top Hits | Small Molecule Name | Description |
|---|---|---|
| 1 | Homoquinolinic acid | Selective, potent NMDA agonist |
| 2 | L-Cysteinesulfinic acid | NMDA and mGlu agonist |
| 3 | Kynurenic acid | Broad spectrum EAA antagonist |
| 4 | (R)-(+)-HA-966 | NMDA partial agonist/antagonist, acts at glycine site |

TABLE 1-continued

| Top Hits | Small Molecule Name | Description |
|---|---|---|
| 5 | m-Chlorophenylbiguanide hydrochloride | Potent and specific 5-HT3 agonist |
| 6 | Calpeptin | Calpain and cathepsin L inhibitor |
| 7 | Dimaprit dihydrochloride | Standard H2 selective agonist |
| 8 | 8-Hydroxy-DPAT hydrobromide | Selective 5-HT1A agonist. Also has moderate affinity for 5-HT7 |
| 9 | trans-4-Hydroxycrotonic acid | GHB receptor ligand |
| 10 | Fasudil hydrochloride | Inhibitor of cyclic nucleotide dependent- and Rho-kinases |
| 11 | Thioperamide | H3 antagonist and H4 inverse agonist |
| 12 | Retinoic acid | Endogenous retinoic acid receptor agonist. |
| 13 | AM580 | Retinoic acid analog; RARα agonist |
| 14 | TTNPB | Retinoic acid analog; RAR agonist |
| 15 | Remoxipride hydrochloride | Selective D2-like antagonist |
| 16 | ICI 215,001 hydrochloride | β3 agonist |
| 17 | Imiloxan hydrochloride | Highly selective α2B antagonist |
| 18 | Spiperone hydrochloride | 5-HT2A antagonist. Also D2-like antagonist |
| 19 | Kenpaullone | Potent cyclin-dependent kinase inhibitor. Also inhibits GSK-3 |
| 20 | CL 218872 | Benzodiazepine agonist |
| 21 | CV 1808 | Non-selective adenosine A2 receptor agonist |
| 22 | Ro 15-4513 | Benzodiazepine partial inverse agonist |
| 23 | Linopirdine dihydrochloride | KCNQ channel blocker |
| 24 | Guggulsterone | Broad spectrum steroid receptor ligand. Antagonizes FXR and displays hypolipidaemic activity |
| 25 | Ch 55 | Potent RAR agonist |
| 26 | 3-MATIDA | Potent, selective mGlu1 antagonist |
| 27 | SEW 2871 | Cell-permeable, selective S1P1 receptor agonist |
| 28 | Immethridine dihydrobromide | Potent H3 agonist, highly selective over H4 |
| 29 | LY 364947 | Selective inhibitor of TGF-βRI |
| 30 | Tranylcypromine hydrochloride | Irreversible inhibitor of MAO-A, MAO-B and LSD1 |
| 31 | (−)-Cytisine | Potent, selective neuronal nicotinic agonist |
| 32 | Nilutamide | Androgen receptor antagonist. Orally active |

TABLE 2

| Well | Small Molecule Name | Replicate Name | Tubb3 | MAP2 | TH1 | KCNJ6 (GRK2) | EN1 | SLC6A3 (DAT) | DDC (AADC) | Pax2 | NR4A2 (NURR1) | PITX3 | LMX1B |
|---|---|---|---|---|---|---|---|---|---|---|---|---|---|
| A09 | Homoquinolinic acid | 1-A09 | 2.95 | 10.03 | 10.77 | 1.76 | 4.83 | 19.18 | 20.19 | 0.05 | 1.99 | 0.4 | 2.32 |
| A10 | L-Cysteinesulfinic acid | 1-A10 | 3.41 | 9.52 | 7.84 | 3.02 | 5.76 | 1.54 | 17.27 | 0.22 | 2.02 | | 2.66 |
| B02 | Kynurenic acid | 1-B02 | 6.43 | 9.12 | 16.8 | 0.07 | 9.25 | 3.41 | 37.45 | 1.16 | 0.27 | | 6.36 |
| B10 | (R)-(+)-HA-966 | 1-B10 | 5.61 | 10.66 | 6.75 | 1.02 | 7.26 | 26.39 | 104.03 | 4.7 | 3.91 | 0.23 | 3.94 |
| G02 | m-Chlorophenylbiguanide hydrochloride | 1-G02 | 4.97 | 9.6 | 6.67 | 1.65 | 7.96 | 1.53 | 69.41 | 0.28 | 5.51 | | 3.73 |
| G05 | Calpeptin | 1-G05 | 6.1 | 12.86 | 15.21 | 4.43 | 6.93 | 6.57 | 295.26 | 3.54 | 2.45 | 0.37 | 2.9 |
| A06 | Dimaprit dihydrochloride | 2-A06 | 9.62 | 12.43 | 9.02 | 0.16 | 15.52 | | 31.92 | | 1.87 | 0.45 | |
| B05 | 8-Hydroxy-DPAT hydrobromide | 2-B05 | 7.8 | 14.43 | 7.32 | 0.9 | 11.69 | 19.9 | 124.29 | 1.25 | 7.66 | | 5.42 |
| B08 | trans-4-Hydroxycrotonic acid | 2-B08 | 10.76 | 12.37 | 13.23 | 0.22 | 12.74 | 6.11 | 69.74 | | 4.49 | | |
| B09 | Fasudil hydrochloride | 2-B09 | 5.67 | 11.62 | 5.53 | 1.57 | 8.69 | 2.79 | 32.39 | 0.27 | 4.53 | 0.27 | 3.5 |
| G04 | Thioperamide | 2-G04 | 5.6 | 13.22 | 8.38 | 2.21 | 7.72 | 25.46 | 95.6 | 1.15 | 3.43 | 0.28 | 3.81 |
| A05 | Retinoic acid | 3-A05 | 7.05 | 7.7 | 1.99 | 2.8 | 12.85 | 1.99 | 110.13 | 0.5 | 152.96 | 0.04 | 1.25 |
| D07 | AM580 | 3-D07 | 4.58 | 8.55 | 5.28 | 2.73 | 12.94 | 0.66 | 81.43 | 0.1 | 7.11 | | 2.16 |
| D08 | TTNPB | 3-D08 | 4.64 | 6.36 | 5.5 | 0.69 | 9.42 | 0.5 | 21.95 | 0.09 | 14.8 | | 1.45 |
| D02 | Remoxipride hydrochloride | 4-D02 | 5.73 | 11.49 | 12.01 | 0.93 | 6.6 | 6.41 | 13.8 | 0.86 | 3.21 | 0.69 | 3.16 |
| E02 | ICI 215,001 hydrochloride | 4-E02 | 5.54 | 11.2 | 6.04 | 1.48 | 8.52 | 1.77 | 29.34 | 39.43 | 2.88 | | 4.79 |
| G09 | Spiperone hydrochloride | 4-G09 | 3.57 | 9.66 | 11.07 | 0.24 | 7.4 | 1.25 | 13.14 | | 0.58 | 0.18 | |
| G05 | Kenpaullone | 6-G05 | 9.61 | 8.17 | 2.15 | 0.12 | 10.97 | 107.85 | 11.12 | | 0.05 | | |
| B09 | CL 218872 | 8-B09 | 4.3 | 8.94 | 13.89 | 0.43 | 5.69 | 0.98 | 8.73 | 0.09 | 1.79 | 0.08 | 2.52 |
| B10 | CV 1808 | 8-B10 | 3.86 | 8.66 | 12.51 | 0.36 | 5.56 | 0.94 | 16.69 | | 1.56 | 0.7 | |
| A03 | Ro 15-4513 | 9-A03 | 4.9 | 7.19 | 8.49 | 0.09 | 5.9 | 0.46 | 12.88 | | 0.9 | 0.72 | |
| A04 | Linopirdine dihydrochloride | 9-A04 | 3.74 | 7.02 | 8.61 | 0.16 | 4.06 | 0.28 | 7.02 | 0.3 | 0.69 | 0.26 | 2.84 |
| B05 | Guggulsterone | 9-B05 | 6.83 | 9.05 | 10.58 | 0.01 | 10.01 | 1.03 | 9.82 | 0.03 | 0.53 | 0.48 | 6.45 |
| B08 | Ch 55 | 9-B08 | 3.48 | 5.25 | 1.19 | 0.25 | 11.61 | 0.11 | 22.86 | 0.06 | 77.93 | 0.13 | 1.54 |
| G03 | 3-MATIDA | 9-G03 | 3.74 | 10.7 | 5.1 | 1.21 | 7.3 | 1.42 | 80.55 | 0.65 | 3.06 | 0.46 | 2.99 |

TABLE 2-continued

| Well | Small Molecule Name | Replicate Name | Tubb3 | MAP2 | TH1 | KCNJ6 (GRK2) | EN1 | SLC6A3 (DAT) | DDC (AADC) | Pax2 | NR4A2 (NURR1) | PITX3 | LMX1B |
|---|---|---|---|---|---|---|---|---|---|---|---|---|---|
| B03 | SEW 2871 | 10-B03 | 5.17 | 12.34 | 7.6 | 0.88 | 8.08 | 32.09 | 68.3 | 1.59 | 2.36 | | 3.65 |
| C08 | Immethridine dihydrobromide | 10-C08 | 10.62 | 12.69 | 9.72 | 0.22 | 11.79 | 33.65 | 28.18 | 41.22 | 0.52 | | 7.66 |
| B05 | LY 364947 | 12-B05 | 4.23 | 10.48 | 5.23 | 1.09 | 7.42 | 5.08 | 64.48 | | 3.01 | | |
| G08 | Nilutamide | 14-G08 | 3.81 | 10.62 | 10.06 | 2.1 | 5.33 | 2.07 | 171.67 | 0.9 | 1.43 | 0.27 | 2.55 |

Although the invention has been described with reference to the above example, it will be understood that modifications and variations are encompassed within the spirit and scope of the invention. Accordingly, the invention is limited only by the following claims.

What is claimed is:

1. A method of producing neural stem cells (NSCs) comprising: (a) treating human pluripotent stem cells (hPSCs) with a checkpoint kinase 1 (CK1) inhibitor and a bone morphogenic protein (BMP) inhibitor; and (b) analyzing the cells for neural stem cell markers, wherein the CK1 inhibitor is SB218078 and the BMP inhibitor is Dorsomorphin, DMH-1 or LD-193189.

2. The method of claim 1, wherein the neural stem cell markers are selected from the group consisting of: BRN2, CD113, CD15, CXCR4, DCX, FABP7, FOXA2, FOXO4, GFAP, LMX1A, Musashi-1, MAP2, Nestin, OTX2, PAX6, TUBB3, SOX1, SOX2, SOX3 and ST6GALNAC5 or any combination thereof.

* * * * *